(12) United States Patent
Meyer et al.

(10) Patent No.: US 9,487,752 B2
(45) Date of Patent: Nov. 8, 2016

(54) PRIMING OF PLURIPOTENT STEM CELLS FOR NEURAL DIFFERENTIATION

(75) Inventors: Nathan Meyer, Mazomanie, WI (US); Matthew George, Fitchburg, WI (US); Casey Stankewicz, Madison, WI (US); Deepika Rajesh, Madison, WI (US)

(73) Assignee: Cellular Dynamics International, Inc., Madison, WI (US)

( * ) Notice: Subject to any disclaimer, the term of this patent is extended or adjusted under 35 U.S.C. 154(b) by 0 days.

(21) Appl. No.: 13/435,698

(22) Filed: Mar. 30, 2012

(65) Prior Publication Data

US 2012/0276063 A1    Nov. 1, 2012

Related U.S. Application Data

(60) Provisional application No. 61/469,527, filed on Mar. 30, 2011.

(51) Int. Cl.

| | |
|---|---|
| *C12Q 1/04* | (2006.01) |
| *A61P 25/00* | (2006.01) |
| *C12N 5/079* | (2010.01) |
| *A61K 35/30* | (2015.01) |
| *C12N 5/0793* | (2010.01) |
| *A61K 35/12* | (2015.01) |

(52) U.S. Cl.
CPC .......... *C12N 5/0619* (2013.01); *A61K 35/12* (2013.01); *A61K 35/30* (2013.01); *C12N 5/0622* (2013.01); *C12N 2501/119* (2013.01); *C12N 2501/155* (2013.01); *C12N 2506/45* (2013.01)

(58) Field of Classification Search
None
See application file for complete search history.

(56) References Cited

U.S. PATENT DOCUMENTS

| | | | |
|---|---|---|---|
| 6,277,820 | B1 | 8/2001 | Rosenthal et al. |
| 6,602,711 | B1 | 8/2003 | Thomson et al. |
| 7,727,762 | B2 | 6/2010 | Fukuda et al. |
| 7,763,464 | B2 | 7/2010 | Xu |
| 7,781,214 | B2 | 8/2010 | Smith et al. |
| 2002/0168766 | A1 | 11/2002 | Gold et al. |
| 2003/0211603 | A1 | 11/2003 | Earp et al. |
| 2007/0238170 | A1 | 10/2007 | Thomson et al. |
| 2008/0038820 | A1 | 2/2008 | Rudy-Reil |
| 2008/0044901 | A1 | 2/2008 | Sasai |
| 2008/0113433 | A1 | 5/2008 | Robins et al. |
| 2008/0171385 | A1 | 7/2008 | Bergendahl et al. |

(Continued)

FOREIGN PATENT DOCUMENTS

| | | |
|---|---|---|
| CN | 101831401 | 9/2010 |
| EP | 1783205 A1 * | 5/2007 |

(Continued)

OTHER PUBLICATIONS

Chambers, Stuart M.; et al; "Highly efficient neural conversion of human ES and iPS cells by dual inhibition of SMAD signaling" Nature Biotechnology, 27, 275-281, 2009.*

(Continued)

*Primary Examiner* — Renee Claytor
*Assistant Examiner* — David Berke-Schlessel
(74) *Attorney, Agent, or Firm* — Parker Highlander PLLC

(57) ABSTRACT

Methods and composition for differentiation of pluripotent stem cells are provided. For example, in certain aspects methods including priming stem cells for neural differentiation in a culture medium essentially free of growth factors such as FGF and TGFβ. As an advantage, the neural cells may be provided with improved consistency and purity.

27 Claims, 4 Drawing Sheets

(56) References Cited

U.S. PATENT DOCUMENTS

| | | |
|---|---|---|
| 2008/0226558 A1 | 9/2008 | Keller et al. |
| 2008/0254003 A1 | 10/2008 | Passier et al. |
| 2009/0047739 A1 | 2/2009 | Gold et al. |
| 2010/0093091 A1 | 4/2010 | Reubinoff |
| 2011/0097799 A1 | 4/2011 | Stankewicz et al. |
| 2011/0117645 A1 | 5/2011 | Yasuda et al. |
| 2011/0129922 A1 | 6/2011 | Fukuda et al. |
| 2012/0129211 A1 | 5/2012 | Kattman et al. |

FOREIGN PATENT DOCUMENTS

| | | |
|---|---|---|
| EP | 2 014 766 | 1/2009 |
| JP | 2-501535 | 5/1990 |
| JP | 2010-162024 | 7/2010 |
| KR | 10-2009-0090586 | 8/2009 |
| WO | WO 89-02459 | 3/1989 |
| WO | WO 01/51616 | 7/2001 |
| WO | WO 03/004626 | 1/2003 |
| WO | WO 2004-015077 | 2/2004 |
| WO | WO 2004-081172 | 9/2004 |
| WO | WO 2005-021720 | 3/2005 |
| WO | WO 2005-123902 | 12/2005 |
| WO | WO 2007/002136 | 1/2007 |
| WO | WO 2008/035110 | 3/2008 |
| WO | WO 2008/106771 | 9/2008 |
| WO | WO 2008-150030 | 12/2008 |
| WO | WO 2009/120762 | 10/2009 |
| WO | WO 2009-123349 | 10/2009 |
| WO | WO 2010/007031 | 1/2010 |
| WO | WO 2010-042669 | 4/2010 |
| WO | WO 2010/063848 | 6/2010 |
| WO | WO 2010-099539 | 9/2010 |
| WO | WO 2013-067362 | 5/2013 |

OTHER PUBLICATIONS

Watanabe, Kiichi; et al; "A ROCK inhibitor permits survival of dissociated human embryonic stem cells" Nature Biotechnology, 25, 681-686, 2007.*

Klim, Joseph R; et al; "A defined glycosaminoglycan-binding substratum for human pluripotent stem cells" Nature Methods, 7, 989-994, 2010.*

Ludwig, Tenneille E; et al; "Derivation of human embryonic stem cells in defined conditions" Nature Biotechnology, 24, 185-187, 2006.*

Bendall, Sean C; et al; "IGF and FGF cooperatively establish the regulatory stem cell niche of pluripotent human cells in vitro" Nature, 448, 1015-1021, 2007.*

Schultz, Thomas C; et al; "Differentiation of Human Embryonic Stem Cells to Dopaminergic Neurons in Serum-Free Suspension Culture" Stem Cells, 22, 1218-1238, 2004.*

Amit, M; et al; "Feeder Layer- and Serum-Free Culture of Human Embryonic Stem Cells" Biology of Reproduction, 70, 837-845, 2004.*

Bauwens et al., "Control of human embryonic stem cell colony and aggregate size heterogeneity influences differentiation trajectories," Stem Cells, 26(9):2300-10, 2008.

Bendall et al., "An enhanced mass spectrometry approach reveals human embryonic stem cell growth factors in culture," Molecular & Cellular Proteomics, 8:421-432, 2009.

Boheler et al., "Differentiation of pluripotent embryonic stem cells into cardiomyocytes," Circulation Research, 91:189, 2002.

Carpenedo et al., "Rotary suspension culture enhances the efficiency, yield, and homogeneity of embryoid body differentiation," Stem Cells, 25(9):2224-34, 2007.

Chen et al., "Chemically defined conditions for human iPSC derivation and culture," Nature Methods 8:424-429, 2011.

Chen et al., "Integration of external signaling pathways with the core transcriptional network in embryonic stem cells," Cell, 133:1106-1117, 2008.

Claassen et al., "ROCK inhibition enhances the recovery and growth of cryopreserved human embryonic stem cells and human induced pluripotent stem cells," Mol. Reprod. Dev., Epub ahead of print, Feb. 20, 2009.

Cohen et al., "The role of FGF-signaling in early neural specification of human embryonic stem cells," Developmental Biology, 340:450-458, 2010.

Gai et al., "Generation and characterization of functional cardiomyocytes using induced pluripotent stem cells derived from human fibroblasts," Cell Biology International, 33:1184-1193, 2009.

Greber et al., "FGF signaling inhibits neural induction in human embryonic stem cells," The EMBO Journal, 30:4874-4884, 2011.

Greber et al., "Fibroblast growth factor 2 modulates transforming growth factor beta signaling in mouse embryonic fibroblasts and human ESCs (hESCs) to support hESC self-renewal," Stem Cells, 25:455-464, 2007.

Hao et al., "Dorsomorphin, a selective small molecule inhibitor of BMP signaling, promotes cardiomyogenesis in embryonic stem cells," PLoS One, 3(8):e2904, 2008. 8 pages.

Harb et al., "The Rho-Rock-Myosin signaling axis determines cell-cell integrity of sel-renewing pluripotent stem cells," PLoS One, 3(8):e3001, 2008.

Kim et al, "Dopamine neurons derived from embryonic stem cells function in an animal model of Parkinson's disease," Nature, 418:50-56, 2002.

Kim et al., "Use of long-term cultured embryoid bodies may enhance cardiomyocyte differentiation by BMP2," Yonsei Med. J., 49(5):819-827, 2008.

Krawetz et al., "Human embryonic stem cells: caught between a ROCK inhibitor and a hard place," Bioessays, 31(3):336-43, 2009.

Krencik and Zhang, "Directed differentiation of functional astroglial subtypes from human pluripotent stem cells," Nature Protocols 6(11):1710-1717, 2011.

Krencik et al., "Specification of transplantable astroglial subtypes from human pluripotent stem cells," Nature Biotechnology 29:528-534, 2011.

Laflamme et al., "Cardiomyocytes derived from human embryonic stem cells in pro-survival factors enhance function of infracted rat hearts," Nature Biotechnology, 25(9):1015-24, 2007.

Lev et al., "Differentiation pathways in human embryonic stem cell-derived cardiomyocytes," Ann. N.Y. Acad. Sci., 1047:50-65, 2005.

Li et al., "Rapid induction and long-term self-renewal of primitive neural precursors from human embryonic stem cells by small molecule inhibitors," PNAS, 108(20):8299-8304, 2011.

Mauritz et al., "Generation of functional murine cardiac myocytes from induced pluripotent stem cells," Circulation, 118:507-517, 2008.

Narazaki et al., "Directed and systematic differentiation of cardiovascular cells from mouse induced pluripotent stem cells," Circulation, 118(5):498-506, 2008.

Niebruegge et al., "Cardiomyocyte production in mass suspension culture: embryonic stem cells as a source for great amounts of functional cardiomyocytes," Tissue Engineering: Part A, 14(10):1591-1601, 2008.

Niebruegge et al., "Generation of human embryonic stem cell-derived mesoderm and cardiac cells using size-specified aggregates in an oxygen-controlled bioreactor," Biotechnology and Bioengineering, 102(2):493-507, 2009.

Ogawa et al., "Activin-Nodal signaling is involved in propagation of mouse embryonic stem cells," J. Cell Sci., 120:55-65, 2007.

Pandur, "What does it take to make a heart," Biology of the Cell, 97:197-210, 2005.

PCT International Search Report and Written Opinion issued in International Application No. PCT/US2012/031457, mailed Sep. 25, 2012.

Pucéat, "Protocols for cardiac differentiation of embryonic stem cells," Methods, 45:168-171, 2008.

Sargent et al., "Cardiomyogenic differentiation of embryoid bodies is promoted by rotary orbital suspension culture," Tissue Engineering: Part A, 15(2):331-342, 2009.

(56) References Cited

OTHER PUBLICATIONS

Sarkar et al., "Targeted proteomics of the secretory pathway reveals the secretome of mouse embryonic fibroblasts and human embryonic stem cells," *The American Society for Biochemistry and Molecular Biology, Inc.*, MCP Papers in Press, Manuscript M112.020503, Sep. 15, 2012.

Smukler et al., "Embryonic stem cells assume a primitive neural stem cell fate in the absence of extrinsic influences," *The Journal of Cell Biology*, 172(1):79-90, 2006.

Stavridis et al., "A discrete period of FGF-induced Erk1/2 signalling is required for vertebrate neural specification," *Development*, 134:2889-2894, 2007.

Sterneckert et al., "Neural induction intermediates exhibit distinct roles of Fgf signaling," *Stem Cells*, 28:1772-1781, 2010.

Suzuki et al., "Nanog binds to Smad1 and blocks bone morphogenetic protein-induced differentiation of embryonic stem cells," *Proc. Natl. Acad. Sci. USA*, 103:10294-10299., 2006.

Takei et al., "Bone morphogenetic protein-4 promotes induction of cardiomyocytes from human embryonic stem cells in serum-based embryoid body development," *Am. J. Physiol. Heart Circ. Physiol.*, 296:H1793-H1803, 2009.

Tropepe et al., "Direct neural fate specification from embryonic stem cells: a primitive mammalian neural stem cell stage acquired through a default mechanism," *Neuron*, 20:65-78, 2001.

Ungrin et al., "Reproducible, ultra high-throughput formation of multicellular organization from single cell suspension-derived embryonic cell aggregates," *PLoS One*, 3(2):e1565, 2008.

Watabe and Miyazono, "Roles of TGF-beta family signaling in stem cell renewal and differentiation," *Cell Res.*, 19:103-115, 2009.

Xu et al., "Characterization and enrichment of cardiomyocytes derived from human embryonic stem cells," *Circulation Research*, 91:501-508, 2002.

Xu et al., "NANOG is a direct target of TGFbeta/activin-mediated SMAD signaling in human ESCs," *Cell Stem Cell*, 3:196-206., 2008.

Zandstra et al., "Scalable production of embryonic stem cell-derived cardiomyocytes," *Tissue Engineering*, 9(4):767-778, 2003.

Zhang et al., "[Differentiating into endothelioid cells from murine embryonic stem cell]," *Zhongguo Xiu Fu Chong Jian Wai Ke Za Zhi*, 23(1):82-86, 2009. (English abstract).

Zhang et al., "Functional cariomyocytes derived from human induced pluirpotent stem cells," *Circulation Research*, 104:e30-e41, 2009.

Bissonnette et al., "The controlled generation of functional basal forebrain cholinergic neurons from human embryonic stem cells," *Stem Cells*, 29:802-811, 2011.

Extended European Search Report issued in European Application No. 12764571.1, mailed Nov. 13, 2014.

Lee et al., "Isolation and directed differentiation of neural crest stem cells derived from human embryonic stem cells," *Nature Biotechnology*, 25(12):1468-1475, 2007.

Li et al., "Specification of motoneurons from human embryonic stem cells," *Nature Biotechnology*, 23(2):215-221, 2005.

Nistor et al., "Human embryonic stem cells differentiate into oligodendrocytes in high purity and myelinate after spinal cord transplantation," *GLIA*, 49:385-396, 2005.

PCT International Preliminary Report on Patentability issued in International Application No. PCT/US2012/031457, mailed Aug. 5, 2013.

Yabut and Bernstein, "The promise of human embryonic stem cells in aging-associated diseases," *Aging*, 3(5):494-508, 2011.

Yan et al., "Directed differentiation of dopaminergic neuronal subtypes from human embryonic stem cells," *Stem Cells*, 23:781-790, 2005.

Office Action issued in Japanese Application No. 2014-502837, mailed Mar. 30, 2016, and English language translation thereof.

\* cited by examiner

| | Example 3 Process (no inhibitors) | SB43 & Dorso added | SB43 only added | Dorso only added |
|---|---|---|---|---|
| Cells per NaCit T150 | 37.3M | 24.6M | 29.8M | 25.1M |
| Cells seeded/T25 | 5M x 4 | 5M x 4 | 5M x 4 | 5M x 4 |
| Ave. Flask Count (D14) | Failed by day 9 | 2.1 M | 10.1 M | 1.4 M |
| Cells plated (D14) | | 2M/well | 2M/well | 1.7M/well |
| Ave. well count (D21) | | 4.6 M/well | 2.6 M/well | 2.1 M/well |
| Cells plated (D21) | | 2.7M/well | 2.7M/well | 2.7M/well |
| %BIII+/Nestin- (D28) | | 91% | 97% | 95% |

FIG. 3C

PRIMING OF PLURIPOTENT STEM CELLS FOR NEURAL DIFFERENTIATION

BACKGROUND OF THE INVENTION

This application claims priority to U.S. Application No. 61/469,527 filed on Mar. 30 2011, the entire disclosure of which is specifically incorporated herein by reference in its entirety without disclaimer.

1. Field of the Invention

The present invention relates generally to the field of stem cell development. More particularly, it concerns production of neural cells from pluripotent stem cells.

2. Description of Related Art

Pluripotent stem cells, such as induced pluripotent stem cells (iPS) cells, are a potential source of cells for production of differentiated cells representative of all cell types of an organism. Differentiation of pluripotent stem cells can be achieved either spontaneously or upon induction.

However, a number of obstacles have stood in the way of developing a paradigm for obtaining substantially enriched populations of specific lineage cells from pluripotent stem cells. Most current approaches involve the formation of embryoid bodies (i.e., cell aggregate) from pluripotent cells in a manner that is not controlled and does not result in homogeneous populations. Mixed cell populations such as those in embryoid bodies of this type are generally unlikely to be suitable for therapeutic or commercial use. Additional problems ensue from the relative fragility of pluripotent cells of primate origin, the difficulty in culturing them, their exquisite sensitivity and dependence on various factors present in the culture environment, and low efficiency and wide variation of differentiation methods.

In particular, it has not been possible to control the differentiation of pluripotent cells in vitro, to provide homogeneous populations of neural cells. In addition, many current methods have relied upon the expression of foreign genes to drive neural differentiation of pluripotent stem cells (Kim et al, 2002). These limitations have restricted the ability to form essentially homogeneous populations of neural cells in vitro, and have restricted their further development for therapeutic and commercial applications.

Thus, there is a need to improve neural differentiation of pluripotent stem cells, especially for large-scale or high efficiency production.

SUMMARY OF THE INVENTION

The present embodiments overcome a major deficiency in the art by providing methods for differentiating pluripotent stem cells into neural cells, especially for high efficiency and large scale production to meet the needs in clinical applications.

Procedures for differentiating pluripotent stem cells preferably employ culture conditions that attempt to mimic the in vivo environment driving the development of a particular lineage, such as by the addition of specific growth factors. When differentiated in vitro, a number of sources may contribute to the growth factor environment, including: 1) endogenous expression from the cells themselves, 2) the sera and/or media that the pluripotent stem cells are cultured and/or subsequently differentiated in, and 3) the addition of exogenous growth factors.

Culture of stem cells under ill-defined conditions can inhibit the effectiveness of maintaining cells in a pluripotent state and reduce reproducibility of differentiation protocols. Therefore, pluripotent cells have been expanded and maintained in an essentially undifferentiated state under a defined medium (e.g., using a TeSR2 or mTeSR1 medium) prior to differentiation of the pluripotent cells.

However, in certain aspects of the present invention it was found that when the pluripotent stem cells were grown on a maintenance medium such as TeSR continuously up to the time the differentiation started, the yield of neurons was incredibly variable. Two growth factors in the TeSR medium, bFGF and TGFβ, were identified that appear to influence the differentiation potential of the cells. When the pluripotent stem cells were "primed," i.e., treated differently prior to the start of aggregate formation (while cells were still in adherent culture), the cells then subsequently behaved differently when further differentiated. In the Examples, when "primed" in the absence of TeSR growth factors, i.e., cultured in any medium that does not have basic fibroblast growth factor (bFGF) and transforming growth factor β (TGFβ), for several days prior to aggregate formation, the cells developed into the neural lineage with surprising purity, rapidity and consistency. Without wishing to be bound by theory, it appears that neural differentiation may be a default lineage, but one may need to reduce the influence that prevents cells from the default neural lineage differentiation (such as avoiding the TeSR medium growth factors bFGF and TGF β) prior to aggregate formation in order to enable the cells to follow the default differentiation route.

Thus, herein is provided a method for producing neural cells. The method may comprise a priming step prior to aggregate formation, for example by culturing the pluripotent stem cells in a medium (i.e., a priming medium) that is essentially free of the externally added growth factors bFGF and TGFβ that reduce neural differentiation. This novel priming step may enhance the neural efficiency and obviate the need of lineage purification for enriching neural lineage cells.

In a particular embodiment, "prior to differentiation" may mean that cells are in an adherent culture while maintaining pluripotent stem cell appearances. Differentiation may initiate when the cells are transferred from the adherent culture into a condition suitable for aggregate formation or cultured adherently in priming media lacking bFGF or TGFβ.

For example, the priming step may involve the transfer of cells into a priming medium gradually (e.g., reducing the growth factors in the culture medium by adding the priming medium over time) or transfer of cells to a priming medium at passage. After the priming step, the method may further comprise differentiating the primed cells into a cell population comprising neural cells, thereby producing neural cells.

The process may comprise forming aggregates from the primed cells in a suspension culture and further differentiating the aggregates into a cell population comprising neural cells. The method may further comprise differentiating the cells into a second population comprising astrocytes. The astrocytes may be enriched or isolated. The astrocyte differentiation may use any reagents known in the art suitable, such as serum or growth factors. In some aspects, the astrocyte differentiation in this method may generate a cell population comprising astrocytes of at least about 50%, 80%, 90%, 95%, 99% or any range derivable therein at a time prior to day 30, 40, 50, 60, 70, 80, 90, 100 or any range derivable therein. In the method of astrocyte differentiation, the culturing media of priming, aggregate formation and/or further differentiation may be in the presence or absence of externally added FGF8 and TGFβ superfamily signaling inhibitor(s).

To minimize non-neural differentiation and increase purity of neural cells, any of the culture media, such as the priming medium, aggregate formation medium, or neural differentiation medium may be essentially free of the externally added growth factors bFGF and TGFβ (including the addition of TGFβ superfamily signaling modulators). The medium may also be essentially free of serum and/or serum-derived growth factors. In a further embodiment, the medium may have or be essentially free of externally added TGFβ superfamily signaling modulators, including positive modulators or inhibitors of BMP signaling and/or Activin/Nodal/TGFβ/GDF signaling. For example, a BMP signaling inhibitor may be dorsomorphin and an Activin/Nodal/TGFβ/GDF signaling inhibitor may be SB431542. In a still further embodiment, the medium may have or be essentially free of other externally added FGF signaling modulators, particularly FGF inhibitors.

Methods may involve the use of pluripotent stem cells as starting material for differentiation, which could be embryonic stem (ES) cells, induced pluripotent stem cells, or embryonic stem cells derived by somatic cell nuclear transfer. In a certain aspect, the pluripotent stem cells may be clonally derived from a single pluripotent stem cell, may comprise a substantial portion of cells clonally derived from a single cell, or may be a pool of multiple populations of cells, wherein each population of cells is clonally derived from a single cell. In a particular aspect, the pluripotent stem cells may be a population of cells, for example, derived from a single cell.

An exemplary process for obtaining pluripotent stem cells from a single cell may comprise incubating a single pluripotent stem cell in medium comprising a ROCK inhibitor or a myosin II inhibitor (e.g., blebbistatin) under conditions to promote cell growth, such as being incubated under adherent culture conditions. Prior to growing the pluripotent stem cells in the suspension culture for aggregate formation, the single pluripotent stem cell as the originating source may be passaged once, twice, three times, four times, or preferably at least five times. In another aspect, the pluripotent stem cells may also be derived from an iPS cell population comprising more than a single cell. The cells may be human, mouse, or other mammalian cells.

Prior to differentiation, the pluripotent stem cells may be cultured on a non-cellular matrix component. Non-limiting examples of the matrix component may include collagen, gelatin, poly-L-lysine, poly-D-lysine, poly-D-ornithine, laminin, and fibronectin and mixtures thereof, for example, protein mixtures from Engelbreth-Holm-Swarm mouse sarcoma cells (such as Matrigel™ or Geltrex) and lysed cell membrane preparations (Klimanskaya et al., 2005). To eliminate variation introduced by uncharacterized components, the medium may be essentially free of externally added animal-derived components, such as serum, feeder cells, or animal-derived proteins, wherein the animal is not a human.

The medium may be chemically defined or undefined (i.e., containing externally added, chemically undefined components). A defined medium will have known quantities and chemical compositions of all ingredients. An undefined medium may have some undefined components, like some complex ingredients, such as cellular extract, which consist of a mixture of chemical species in unknown proportions. In a particular example, the defined medium may be based on Dulbecco's Modified Eagle Medium (DMEM), such as a DMEM medium with nutrient mixture F-12 (DMEM/F 12), a DMEM/F 12 medium with N2 supplement, a DMEM-F12 medium with B-27 supplement, or a DMEM-F12 medium with an insulin, transferrin, and selenium (ITS) supplement.

In some aspects, the cells may be cultured in a priming medium for about 4, 8, or 12 hours, 1, 2, 3, 4, 5, 6, 7, 8, 9, or 10 days (or any range derivable therein) prior to aggregate formation. The cells may be cultured in a priming medium volume of about 5, 10, 15, 20, 25, 30, 50, 100, 150, 200, 250, 300, 350, 400, 450, 500 mL, or any range derivable therein. The cells may be cultured in a priming medium that is replaced every 4, 8, or 12 hours, 1, 2, 3, 4, 5 days, or any range derivable therein. In certain aspects, the cells may be cultured in a priming medium for a priming period. The priming period may be a defined time period or a time period identified by optimization for a selected pluripotent stem cell line or clone or other specified condition(s). For example, the defined priming period may start from about 4, 8, or 12 hours, 1, 2, 3, 4, 5, 6, 7, 8, 9, or 10 days (or any range derivable therein) prior to differentiation or any range derivable therein. The priming period may last about 4, 8, or 12 hours, 1, 2, 3, 4, 5, 6, 7, 8, 9, or 10 days, or continue up to the time when further differentiation starts (any intermediate time period may also be included).

In further aspects, the methods may further comprise culturing the pluripotent stem cells or progeny cells thereof in the presence of a determined amount of externally added TGFβ superfamily signaling inhibitor and/or FGF8. Such culturing may be any time in the steps of priming (culturing prior to aggregate formation), forming aggregates, or further differentiation. In a particular aspect, the cells may be cultured at most about one, two, three, four, five, six days (or any range derivable therein) during priming and/or during aggregate formation in the presence of a determined amount of externally added TGFβ superfamily signaling inhibitor and/or FGF8. In a further particular aspect, the cells may be cultured at most about the first one, two, three, four, five, six, seven, eight, nine, ten days (or any range derivable therein) of further differentiation after aggregate formation in the presence of a determined amount of externally added TGFβ superfamily signaling inhibitor and/or FGF8 and then in the subsequent period cultured in the absence of the externally added TGFβ superfamily signaling inhibitor and/or FGF8. In certain aspects, the cells may be cultured in the presence of a determined amount of externally added TGFβ superfamily signaling inhibitor(s) and/or FGF8 during priming, aggregate formation and/or further differentiation. In certain aspects, the cells may be cultured in the absence of externally added TGFβ superfamily signaling inhibitor and/or FGF8 during priming, aggregate formation and/or further differentiation.

Due to line-to-line and clone-to-clone variability, there may be provided methods for determining the appropriate amount of TGFβ superfamily signaling inhibitor and/or FGF8 for neural differentiation of a population of pluripotent stem cells. In a certain aspect, the method may further comprise testing the neural differentiation efficiency of a population of pluripotent stem cells to determine the appropriate amount, if any, of externally added TGFβ superfamily signaling inhibitor(s) and/or FGF8 needed that will result in efficient neural differentiation yielding a neural culture of high purity. The neural differentiation efficiency can be measured in terms of all neurons or neural cell types, such as astrocytes.

The differentiation may start with or without dissociating the pluripotent stem cells. In a preferable embodiment, the differentiation may comprise dissociating the stem cells into an essentially single cell culture. The dissociation encompasses the use of any method known now or later developed that is capable of producing an essentially single cell culture. In an exemplary embodiment, the cells may be dissociated by a protease treatment or a mechanical treatment like pipetting. For example, the protease may be collagenase, trypsin-EDTA, dispase, or a combination thereof. Alternatively, a chelating agent may be used to dissociate the cells, such as sodium citrate, EGTA, EDTA or a combination thereof. An essentially single cell culture may be a cell culture wherein the cells desired to be grown are dissociated from one another, such that the majority of the cells are single cells, or at most two cells that remain associated (doublets). Preferably, greater than 50%, 60%, 70%, 80%, 90%, 95%, 96%, 97%, 98%, 99% or more of the cells desired to be cultured are singlets or doublets.

The differentiation method encompasses the use of any method known now or later developed that is capable of differentiating pluripotent stem cells. The differentiation may involve forming cell aggregates (embryoid bodies) or may not need to form cell aggregates. In a particular embodiment, the dissociated cells may form cell aggregates in a medium (aggregate formation medium). The aggregate formation medium may contain or may be essentially free of TGFβ superfamily signaling modulators and bFGF.

Any of the priming, aggregate formation and/or further differentiation culture media may contain externally added at least or at most from about 5 to about 200 ng/ml FGF8, e.g., at least or about 5, 10, 15, 20, 25, 30, 35, 40, 45, 50, 55, 60, 65, 70, 75, 80, 85, 90, 95, 100, 150, 180, 200 ng/ml or any range derivable therein. Externally added FGF8 or TGFβ superfamily signaling inhibitors may be at an amount of at least, about or at most 5, 10, 15, 20, 25, 30, 35, 40, 45, 50, 55, 60, 65, 70, 75, 80, 90, 100, 150, 200 ng/ml, at least, about, or at most 0.5, 0.6, 0.7, 0.8, 0.9, 1, 1.5, 2, 2.5, 3, 4, 5, 6, 7, 8, 9, 10, 25, 50 µM, or any range derivable therein, or any concentration effective for improving the production of high purity neural cell types.

To promote survival of dissociated cells, the medium may comprise an externally added myosin II inhibitor or Rho-associated kinase (ROCK) inhibitor. The myosin II inhibitor may be blebbistatin. The ROCK inhibitor may be Y27632, HA-100 or H1152. Such inhibitors may have a concentration of about 0.05 to about 50 µM, for example, at least or about 0.05, 0.1, 0.2, 0.5, 0.8, 1, 1.5, 2, 2.5, 5, 7.5, 10, 15, 20, 25, 30, 35, 40, 45, or 50 µM, including any range derivable therein, or any concentration effective for promoting cell growth or survival.

The aggregate formed from the pluripotent stem cells may be about, at least or at most 5, 10, 15, 20, 25, 30, 50, 100, 150, 200, 250, 300, 350, 400, 450, 500 µm in diameter. The diameter may be a mean, median or an average diameter. In another aspect, at least about 20%, 30%, 40%, 50%, 80%, 90%, 95%, or 99% (or any range derivable therein) of the aggregates may comprise at least or about 10, 15, 20, 25, 30, 35, 40, 45, 50, 80, 100, 150, 200, 250, 300, 400, 500, 1000 cells, or any range derivable therein. In certain aspects, a substantial portion (e.g., at least about 50%, 80%, 90%, 95%, 99% or any range derivable therein) of the aggregates are about 80 to 200 µm in diameter. The approximate uniformity of an optimal range of aggregate size may promote differentiation as differentiation is guided by spatial cues and interaction between various cell types, which can be manipulated by varying aggregate size.

The differentiation may comprise culturing pluripotent stem cells and/or progeny cells thereof in an adherent or suspension culture. In a particular embodiment, during differentiation, the cell may be transferred to an adherent culture. For example, the adherent culture may have a non-cellular matrix component. In a preferable embodiment, the methods may be used for differentiation of pluripotent stem cells to produce neural cells in a suspension culture. Pluripotent stem cells or progeny cells thereof may be incubated in a suspension culture. In a further embodiment, pluripotent stem cell aggregates may be formed in a suspension culture. The suspension culture may have a volume of about, at least or at most 2 mL, 5 mL, 10 mL, 20 mL, 30 mL, 40 mL, 50 mL, 100 mL, 200 mL, 500 mL, 1 liters, 3 liters, 5 liters, 10 liters, 20 liters, 25 liters, 30, liters, 40 liters, 50 liters, or any range derivable therein, such as in a bioreactor. Some embodiments involve cells growing in a space whose volume is larger than a standard Petri dish or 96-well plate; consequently, some embodiments exclude the use of such containers.

To optimize the size and growth of the cell aggregates, the suspension culture may be moved at a speed of at least or about 5, 10, 15, 20, 30, 35, 40, 45, 50, 55, 60, 65, 70, 75, 80, 85, 90, 100 rpm, or any range of speed derivable therein. The movement may comprise stirring, shaking, rocking or rotating as non-limiting examples.

The medium used in differentiation may or may not comprise the use of externally added TGFβ superfamily signaling inhibitor(s), bFGF inhibitors, or both. The TGFβ superfamily inhibitor may be a BMP signaling inhibitor and/or Activin/Nodal/TGFβ/GDF signaling inhibitor. A bFGF signaling inhibitor may be PD166866. With the improvement of neural induction by priming, the method may obviate the need to use such inhibitors in differentiation.

In certain aspects, the population of iPS cells or differentiated cells may be clonally derived from a single iPS cell. In a further aspect, there may be provided a cell population of at least or about $10^7$, $10^8$, $10^9$, or up to about $10^{10}$ (or any range derivable therein) cells. The cell population provided may comprise at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100% (or any range derivable therein) cells, such as neural cells. In a particular embodiment, the cell population may comprise at least 90%, 91%, 92%, 93%, 94%, 95%, 96%, 97%, 98%, 99% or 100% (or any range derivable therein) neural cells. This invention may achieve an unexpected high yield of neural cells from differentiation of pluripotent stem cells as compared with currently known methods and methods without the use of priming.

A cell population comprising the neural cells or astrocytes provided by any of the methods above may also be provided. Further embodiments may provide an isolated cell population of at least or about $10^6$, $10^7$, $10^8$, $10^9$, $10^{10}$ neural cells (or any range derivable therein). The differentiated cells may comprise at least 90% (for example, at least or about 90%, 95%, 96%, 97%, 98%, 99%, 99.5%, or any range derivable therein) neural cells or astrocytes. In a specific example, the cell population may contain a transgene (e.g., encoding a selectable and/or screenable marker) under a promoter specific for neural cells. For example, the transgene may be an antibiotic resistance gene or a fluorescent protein-encoding gene. Non-limiting examples of neural-specific promoters include a promoter of doublecortin (DCX), neuronal class III (β-tubulin (TUJ-1), synapsin I (SYN1), enolase 2/neuron-specific enolase (ENO2/NSE), glial fibrillary acidic protein (GFAP), tubulin alpha-1A chain (TUBA1A), or microtubule-associated-protein-2 (MAP-2). The method may further comprise isolating or enriching neural cells or astrocytes, for example, based on the neuron-specific or astrocytes-specific expression of selectable or screenable markers.

In a further embodiment, a method for treating a subject having a neural disease may also be provided. The method may comprise administering to the subject the neural cells or astrocytes provided by the methods described above. The subject may have a neural disease or disorder, including but not limited to Parkinson's disease, Huntington's disease, lysosomal storage diseases, multiple sclerosis, memory and behavioral disorders, Alzheimer's disease, epilepsy, seizures, macular degeneration, and other retinopathies. The cells can also be used in treatment of nervous system injuries that arise from spinal cord injuries, stroke, or other neural trauma or can be used to treat neural disease and damage induced by surgery, chemotherapy, drug or alcohol abuse, environmental toxins and poisoning. The cells may also be useful in treatment of peripheral neuropathy such as those neuropathies associated with injury, diabetes, autoimmune disorders or circulatory system disorders. The cells may also be used to treat diseases or disorders of the neuroendocrine system, and autonomic nervous system including the sympathetic and parasympathetic nervous system. In a preferred embodiment, a therapeutically effective amount of the neural cells or cell culture enriched in neural cells is administered to a patient with a neural disease. As used herein, the term "therapeutically effective amount" refers to that number of cells which is sufficient to at least alleviate one of the symptoms of the neural disease, disorder, nervous system injury, damage or neuropathy. In a preferred embodiment, the neural disease is Parkinson's disease.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan; however, these terms may be used interchangeably with "comprise" or "comprising" respectively.

As used herein in the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 3A-3C: Incorporation of TGFβ superfamily inhibitors dorsomorphin and/or SB-431542 and/or FGF8 during priming and/or early differentiation can improve purities of neurons for certain pluripotent stem cell lines and clones (wp=well plate, N2=DMEM-F12 basal medium with N2 supplement) (FIG. 3A), flow cytometry analysis of Day 27 cells cultured in medium containing TGFβ superfamily inhibitors and/or FGF8 (cells were fed daily not including the last day listed in the table) (FIG. 3B), adding only one TGFβ superfamily inhibitor to culture medium (SB-431542 or dorsomorphin) on Days −2, −1, 0 and 1 can produce neuronal cell purities on Day 28 comparable to addition of both inhibitors to culture medium during the same timeframe (FIG. 3C).

DESCRIPTION OF ILLUSTRATIVE EMBODIMENTS

I. Introduction

Figure 1A:
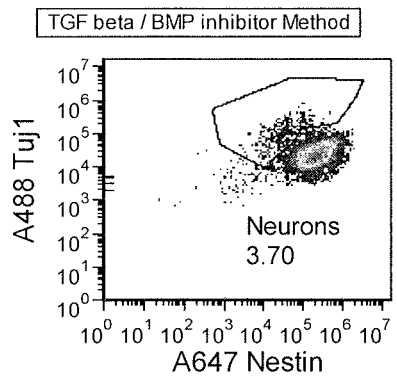
FIGS. 1A-1B: Differentation resulting from a previously published method using Activin/Nodal/TGFβ/GDF and BMP inhibitors resulted in a culture that is 3.7% neurons (FIG. 1A). Resulting culture from N2 primed cells were 95.98% neurons (FIG. 1B). Cultures were analyzed at day 24 of differentation.

A variety of different methods and compositions are described herein. Certain embodiments concern several important advantages that improve the stem cell differentiation process. It has been discovered that neural differentiation potential of pluripotent stem cells may be influenced by stem cells' culture environment prior to differentiation. In some embodiments methods may be developed to increase uniformity and yields of neural cells from differentiation of pluripotent stem cells, particularly by using a priming medium in the absence of growth factors that reduce neural differentiation potential.

"Pluripotency" refers to a stem cell that has the potential to differentiate into all cells constituting one or more tissues or organs, for example, any of the three germ layers: endoderm (interior stomach lining, gastrointestinal tract, the lungs), mesoderm (muscle, bone, blood, urogenital), or ectoderm (epidermal tissues and nervous system).

"Induced pluripotent stem cells," commonly abbreviated as iPS cells or iPSCs, refer to a type of pluripotent stem cell artificially prepared from a non-pluripotent cell, typically an adult somatic cell, or terminally differentiated cell, such as fibroblast, a hematopoietic cell, a myocyte, a neuron, an epidermal cell, or the like, by introducing or contacting with reprogramming factors.

"Embryonic stem (ES) cells" are pluripotent stem cells derived from early embryos.

"Adherent culture," refers to a culture in which cells, or aggregates of cells, are attached to a surface.

"Suspension culture," refers to a culture in which cells, or aggregates of cells, multiply while suspended in liquid medium.

"Essentially free" of an externally added component refers to a medium that does not have, or that have essentially none of, the specified component from a source other than the cells in the medium. "Essentially free" of externally added growth factors or signaling inhibitors, such as TGFβ, bFGF, TGFβ superfamily signaling inhibitors, etc., may mean a minimal amount or an undetectable amount of the externally added component. For example, a medium or environment essentially free of TGFβ or bFGF can contain less than 5, 4, 3, 2, 1, 0.9, 0.8, 0.7, 0.6, 0.5, 0.4, 0.3, 0.2, 0.1, 0.01, 0.001 ng/mL or any range derivable therein. For example, a medium or environment essentially free of signaling inhibitors can contain less than 0.2, 0.1, 0.09, 0.08, 0.07, 0.06, 0.05, 0.04, 0.03, 0.02, 0.01, 0.005, 0.001 µM, or any range derivable therein.

"Rho-associated kinase inhibitors," abbreviated as "ROCK inhibitors," refer to any substance that inhibits or reduces the function of Rho-associated kinase or its signaling pathway in a cell, such as a small molecule, an siRNA, a miRNA, an antisense RNA, or the like. "ROCK signaling pathway," as used herein, may include any signal processors involved in the ROCK-related signaling pathway, such as the Rho-ROCK-Myosin II signaling pathway, its upstream signaling pathway, or its downstream signaling pathway in a cell. Examples of ROCK inhibitors include, but are not limited to, a Rho-specific inhibitor or a ROCK-specific inhibitor.

"Myosin II inhibitors" refer to any substance that inhibits or reduces the function of myosin II or its signaling pathway in a cell, such as a small molecule, an siRNA, a miRNA, an antisense RNA, or the like. Examples of myosin II inhibitors include a MRLC (myosin regulatory light chain)-specific inhibitor or a Myosin II-specific inhibitor.

"Differentiation" is a process by which a less specialized cell forms progeny of at least a new cell type which is more specialized.

The term "aggregate promoting medium" means any medium that enhances the aggregate formation of cells without any restriction as to the mode of action.

The term "aggregates," i.e., embryoid bodies, refers to homogeneous or heterogeneous clusters of cells comprising differentiated cells, partly differentiated cells and/or pluripotent stem cells cultured in suspension.

"Neurons" or "neural cells" or "neural cell types" or "neural lineage" may include any neuron lineage cells, and can be taken to refer to cells at any stage of neuronal ontogeny without any restriction, unless otherwise specified. For example, neurons may include both neuron precursor cells, mature neurons and neural cell types such as astrocytes.

A "gene," "polynucleotide," "coding region," "sequence, " "segment," or "fragment," which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "transgene," refers to a gene, nucleic acid, or polynucleotide which has been introduced into the cell or organism by artificial or natural means, such as an exogenous nucleic acid. An exogenous nucleic acid may be from a different organism or cell, or it may be one or more additional copies of a nucleic acid which occurs naturally within the organism or cell. By way of a non-limiting example, an exogenous nucleic acid is in a chromosomal location different from that of natural cells, or is otherwise flanked by a different nucleic acid sequence than that found in nature.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

II. Sources of Pluripotent Stem Cells

Pluripotent stem cells may be used in present methods for neural induction of pluripotent stem cells. Methods and compositions have been disclosed in the present invention to improve the neural differentiation efficiency by priming the pluripotent stem cells in a condition that improves neural development potential.

The term "pluripotent stem cell" refers to a cell capable of giving rise to cells of all three germinal layers, that is, endoderm, mesoderm and ectoderm. Although in theory a pluripotent stem cell can differentiate into any cell of the body, the experimental determination of pluripotency is typically based on differentiation of a pluripotent cell into several cell types of each germinal layer. In some embodiments of the present invention, a pluripotent stem cell is an embryonic stem (ES) cell derived from the inner cell mass of a blastocyst. In other embodiments, the pluripotent stem cell is an induced pluripotent stem cell derived by reprogramming somatic cells. In certain embodiments, the pluripotent stem cell is an embryonic stem cell derived by somatic cell nuclear transfer.

A. Embryonic Stem Cells

Embryonic stem (ES) cells are pluripotent cells derived from the inner cell mass of a blastocyst. ES cells can be isolated by removing the outer trophectoderm layer of a developing embryo, then culturing the inner mass cells on a feeder layer of non-growing cells. Under appropriate conditions, colonies of proliferating, undifferentiated ES cells are produced. The colonies can be removed, dissociated into individual cells, then replated on a fresh feeder layer. The replated cells can continue to proliferate, producing new colonies of undifferentiated ES cells. The new colonies can then be removed, dissociated, replated again and allowed to grow. This process of "subculturing" or "passaging" undifferentiated ES cells can be repeated a number of times to produce cell lines containing undifferentiated ES cells (U.S. Pat. Nos. 5,843,780; 6,200,806; 7,029,913). A "primary cell culture" is a culture of cells directly obtained from a tissue such as the inner cell mass of a blastocyst. A "subculture" is any culture derived from the primary cell culture.

Methods for obtaining mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be obtained from blastocysts using previously described methods (Thomson et al., 1995; Thomson et al., 1998; Thomson and Marshall, 1998; Reubinoff et al, 2000.) In one method, day-5 human blastocysts are exposed to rabbit anti-human spleen cell antiserum, then exposed to a 1:5 dilution of Guinea pig complement to lyse trophectoderm cells. After removing the lysed trophectoderm cells from the intact inner cell mass, the inner cell mass is cultured on a feeder layer of gamma-inactivated mouse embryonic fibroblasts and in the presence of fetal bovine serum. After 9 to 15 days, clumps of cells derived from the inner cell mass can be chemically (i.e. exposed to trypsin) or mechanically dissociated and replated in fresh medium containing fetal bovine serum and a feeder layer of mouse embryonic fibroblasts. Upon further proliferation, colonies having undifferentiated morphology are selected by micropipette, mechanically dissociated into clumps, and replated (see U.S. Pat. No. 6,833,269). ES-like morphology is characterized as compact colonies with apparently high nucleus to cytoplasm ratio and prominent nucleoli. Resulting ES cells can be routinely passaged by brief trypsinization or by selection of individual colonies by micropipette. In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as Matrigel™ or laminin in the presence of "conditioned" medium containing basic fibroblast growth factor (Xu et al., 2001). The medium is previously conditioned by coculturing with fibroblasts.

Methods for the isolation of rhesus monkey and common marmoset ES cells are also known (Thomson, and Marshall, 1998; Thomson et al., 1995; Thomson and Odorico, 2000).

Another source of ES cells are established ES cell lines. Various mouse cell lines and human ES cell lines are known and conditions for their growth and propagation have been defined. For example, the mouse CGR8 cell line was established from the inner cell mass of mouse strain 129 embryos, and cultures of CGR8 cells can be grown in the presence of LIF without feeder layers. As a further example, human ES cell lines H1, H7, H9, H13 and H14 were established by Thomson et al. In addition, subclones H9.1 and H9.2 of the H9 line have been developed. It is anticipated that virtually any ES or stem cell line known in the art and may be used with the present invention, such as, e.g., those described in Yu and Thomson, 2008, which is incorporated herein by reference.

The source of ES cells for use in connection with the present invention can be a blastocyst, cells derived from culturing the inner cell mass of a blastocyst, or cells obtained from cultures of established cell lines. Thus, as used herein, the term "ES cells" can refer to inner cell mass cells of a blastocyst, ES cells obtained from cultures of inner mass cells, and ES cells obtained from cultures of ES cell lines.

B. Induced Pluripotent Stem Cells

Induced pluripotent stem (iPS) cells are cells which have the characteristics of ES cells but are obtained by the reprogramming of differentiated somatic cells. Induced pluripotent stem cells have been obtained by various methods. In one method, adult human dermal fibroblasts are transfected with transcription factors Oct4, Sox2, c-Myc and Klf4 using retroviral transduction (Takahashi et al., 2007). The transfected cells are plated on SNL feeder cells (a mouse cell fibroblast cell line that produces LIF) in medium supplemented with basic fibroblast growth factor (bFGF). After approximately 25 days, colonies resembling human ES cell colonies appear in culture. The ES cell-like colonies are picked and expanded on feeder cells in the presence of bFGF.

Based on cell characteristics, cells of the ES cell-like colonies are induced pluripotent stem cells. The induced pluripotent stem cells are morphologically similar to human ES cells, and express various human ES cell markers. Also, when grown under conditions that are known to result in differentiation of human ES cells, the induced pluripotent stem cells differentiate accordingly. For example, the induced pluripotent stem cells can differentiate into cells having neuronal structures and neuronal markers. It is anticipated that virtually any iPS cells or cell lines may be used with the present invention, including, e.g., those described in Yu and Thomson, 2008.

In another method, human fetal or newborn fibroblasts are transfected with four genes, Oct4, Sox2, Nanog and Lin28 using lentivirus transduction (Yu et al., 2007). At 12-20 days post infection, colonies with human ES cell morphology become visible. The colonies are picked and expanded. The induced pluripotent stem cells making up the colonies are morphologically similar to human ES cells, express various human ES cell markers, and form teratomas having neural tissue, cartilage and gut epithelium after injection into mice.

Methods of preparing induced pluripotent stem cells from mouse are also known (Takahashi and Yamanaka, 2006). Induction of iPS cells typically require the expression of or exposure to at least one member from the Sox family and at least one member from the Oct family. Sox and Oct are thought to be central to the transcriptional regulatory hierarchy that specifies ES cell identity. For example, Sox may be Sox-1, Sox-2, Sox-3, Sox-15, or Sox-18; Oct may be Oct-4. Additional factors may increase the reprogramming efficiency, like Nanog, Lin28, Klf4, or c-Myc; specific sets of reprogramming factors may be a set comprising Sox-2, Oct-4, Nanog and, optionally, Lin-28; or comprising Sox-2, Oct4, Klf and, optionally, c-Myc.

IPS cells, like ES cells, have characteristic antigens that can be identified or confirmed by immunohistochemistry or flow cytometry, using antibodies for SSEA-1, SSEA-3 and SSEA-4 (Developmental Studies Hybridoma Bank, National Institute of Child Health and Human Development, Bethesda Md.), and TRA-1-60 and TRA-1-81 (Andrews et al., 1987). Pluripotency of embryonic stem cells can be confirmed by injecting approximately $0.5\text{-}10\times10^6$ cells into the rear leg muscles of 8-12 week old male SCID mice. Teratomas develop that demonstrate at least one cell type of each of the three germ layers.

In certain aspects of the present invention, iPS cells are made from reprogramming somatic cells using reprogramming factors comprising an Oct family member and a Sox family member, such as Oct4 and Sox2 in combination with Klf or Nanog as describe above. The somatic cell in certain aspects of the present invention may be any somatic cell that can be induced to pluripotency, such as a fibroblast, a keratinocyte, a hematopoietic cell, a mesenchymal cell, a liver cell, a stomach cell, or a β cell. In a certain aspect, T cells may also be used as source of somatic cells for reprogramming (see U.S. Application No. 61/184,546, incorporated herein by reference).

Reprogramming factors may be expressed from expression cassettes comprised in one or more vectors, such as an integrating vector, a chromosomally non-integrating RNA viral vector (see U.S. application Ser. No. 13/054,022, incorporated herein by reference) or an episomal vector, such as an EBV element-based system (see U.S. Application No. 61/058,858, incorporated herein by reference; Yu et al., 2009). In a further aspect, reprogramming proteins or RNA (such as mRNA or miRNA) could be introduced directly into somatic cells by protein or RNA transfection (see U.S. Application No. 61/172,079, incorporated herein by reference; Yakubov et al., 2010).

C. Embryonic Stem Cells Derived by Somatic Cell Nuclear Transfer

Pluripotent stem cells can be prepared by means of somatic cell nuclear transfer, in which a donor nucleus is transferred into a spindle-free oocyte. Stem cells produced by nuclear transfer are genetically identical to the donor nuclei. In one method, donor fibroblast nuclei from skin fibroblasts of a rhesus macaque are introduced into the cytoplasm of spindle-free, mature metaphase II rhesus macaque ooctyes by electrofusion (Byrne et al., 2007). The fused oocytes are activated by exposure to ionomycin, then incubated until the blastocyst stage. The inner cell mass of selected blastocysts are then cultured to produce embryonic stem cell lines. The embryonic stem cell lines show normal ES cell morphology, express various ES cell markers, and differentiate into multiple cell types both in vitro and in vivo. As used herein, the term "ES cells" refers to embryonic stem cells derived from embryos containing fertilized nuclei. ES cells are distinguished from embryonic stem cells produced by nuclear transfer, which are referred to as "embryonic stem cells derived by somatic cell nuclear transfer."

III. Priming and Differentiation Conditions for Pluripotent Stem Cells

Depending on culture conditions, pluripotent stem cells can produce colonies of differentiated cells or undifferentiated cells. For improved differentiation consistency and efficiency, methods for the use of particular priming conditions for differentiation of pluripotent stem cells are provided. For example, pluripotent stem cells are cultured in a medium essentially free of grow factors like TGFβ and bFGF prior to differentiation, more particularly, prior to the induction of aggregate formation. Unless otherwise specified, differentiation is achieved by induction (e.g., aggregate formation), which may at least involve a change of culture conditions, but not by spontaneous changes.

"Priming" of pluripotent stem cells may mean a period or process prior to the start of aggregate formation, during which pluripotent stem cells may be prepared for desired differentiation. The term "differentiate" means the progression of a cell down a developmental pathway. The term "differentiated" is a relative term describing a cell's progression down a developmental pathway in comparison with another cell. For example, a pluripotent cell can give rise to any cell of the body, while a more differentiated cell such as a hematopoietic cell will give rise to fewer cell types.

Cultures of pluripotent stem cells are described as "undifferentiated" when a substantial proportion (e.g., at least about 50%, 80%, 90%, 95%, 99% or any range derivable therein) of stem cells and their derivatives in the population display morphological characteristics of undifferentiated cells, clearly distinguishing them from differentiated cells of embryo or adult origin. Undifferentiated ES or iPS cells are recognized by those skilled in the art, and typically appear in the two dimensions of a microscopic view in colonies of cells with high nuclear/cytoplasmic ratios and prominent nucleoli. It is understood that colonies of undifferentiated cells can have neighboring cells that are differentiated.

In certain aspects, starting cells for the present methods may comprise at least or about $10^4$, $10^5$, $10^6$, $10^7$, $10^8$, $10^9$, $10^{10}$, $10^{11}$, $10^{12}$, $10^{13}$ cells or any range derivable therein. The starting cell population may have a seeding density of at least or about 10, $10^1$, $10^2$, $10^3$, $10^4$, $10^5$, $10^6$, $10^7$, $10^8$ cells/mL, or any range derivable therein.

A. Medium for Priming and Differentiation

A priming or differentiation medium according to certain aspects of the present invention can be prepared using a medium to be used for culturing animal cells as its basal medium. The priming medium may be a medium essentially free of TGFβ and bFGF. Any of the media used in differentiation may contain TGFβ and bFGF or may be a medium essentially free of TGFβ and bFGF. In certain aspects, the priming medium or the differentiation medium may obviate the need for externally added TGFβ superfamily signaling inhibitors and externally added bFGF inhibitors.

In certain aspects, the priming medium, aggregate formation medium or the medium for further differentiation may contain FGF8 (fibroblast growth factor 8) or inhibitors of TGFβ superfamily signaling, such as SB-431542 or dorsomorphin. In particular aspects, the FGF8 or the TGF superfamily signaling inhibitor(s) may be present in an appropriate amount as determined by a separate experiment for the same batch, line or clone of cells (see U.S. application 61/394,589, incorporated herein by reference).

As the basal medium, any chemically defined medium, such as Eagle's Basal Medium (BME), BGJb, CMRL 1066, Glasgow MEM, Improved MEM Zinc Option, Iscove's modified Dulbecco's medium (IMDM), Medium 199, Eagle MEM, αMEM, DMEM, Ham, RPMI 1640, and Fischer's media, variations or combinations thereof can be used, wherein TGFβ and bFGF may or may not be included.

In further embodiments, the cell priming or differentiation environment can also contain supplements such as B-27 supplement, an insulin, transferrin, and selenium (ITS) supplement, L-Glutamine, NEAA (non-essential amino acids), P/S (penicillin/streptomycin), N2 supplement (5 μg/mL insulin, 100 μg/mL transferrin, 20 nM progesterone, 30 nM selenium, 100 μM putrescine (Bottenstein, and Sato, 1979 PNAS USA 76, 514-517) and β-mercaptoethanol (β-ME). It is contemplated that additional factors may or may not be added, including, but not limited to fibronectin, laminin, heparin, heparin sulfate, retinoic acid.

Growth factors may or may not be added to the priming medium, aggregate formation medium and/or further differentiation medium, such as members of the epidermal growth factor family (EGFs), members of the fibroblast growth factor family (FGFs) including FGF2 and/or FGF8, members of the platelet derived growth factor family (PDGFs), transforming growth factor (TGF)/bone morphogenetic protein (BMP)/growth and differentiation factor (GDF) factor family antagonists including but not limited to noggin, follistatin, chordin, gremlin, cerberus/DAN family proteins, ventropin, and amnionless. TGF, BMP, and GDF antagonists could also be added in the form of TGF, BMP, and GDF receptor-Fc chimeras. Other factors that may or may not be added include molecules that can activate or inactivate signaling through Notch receptor family, including but not limited to proteins of the Delta-like and Jagged families as well as gamma secretase inhibitors and other inhibitors of Notch processing or cleavage such as DAPT. Other growth factors may include members of the insulin like growth factor family (IGF), the wingless related (WNT) factor family, and the hedgehog factor family.

Additional factors may be added in a priming, aggregate formation and/or further differentiation medium to promote neural stem/progenitor proliferation and survival as well as neuron survival and differentiation. These neurotrophic factors include but are not limited to nerve growth factor (NGF), brain derived neurotrophic factor (BDNF), neurotrophin-3 (NT-3), neurotrophin-4/5 (NT-4/5), interleukin-6 (IL-6), ciliary neurotrophic factor (CNTF), leukemia inhibitory factor (LIF), cardiotrophin, members of the transforming growth factor (TGF)/bone morphogenetic protein (BMP)/growth and differentiation factor (GDF) family, the glial derived neurotrophic factor (GDNF) family including but not limited to neurturin, neublastin/artemin, and persephin and factors related to and including hepatocyte growth factor. Neural cultures that are terminally differentiated to form post-mitotic neurons may also contain a mitotic inhibitor or mixture of mitotic inhibitors including but not limited to 5-fluoro 2'-deoxyuridine and cytosine β-D-arabino-furanoside (Ara-C).

The medium can be a serum-containing or serum-free medium. The serum-free medium may refer to a medium with no unprocessed or unpurified serum and accordingly, can include media with purified blood-derived components or animal tissue-derived components (such as growth factors). From the aspect of preventing contamination with heterogeneous animal-derived components, serum can be derived from the same animal as that of the stem cell(s).

The medium may contain or may not contain any alternatives to serum. The alternatives to serum can include materials which appropriately contain albumin (such as lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3'-thiolglycerol, or equivalents thereto. The alternatives to serum can be prepared by the method disclosed in International Publication No. 98/30679, for example. Alternatively, any commercially available materials can be used for more convenience. The commercially available materials include knockout Serum Replacement (KSR), Chemically-defined Lipid concentrated (Gibco), and Glutamax (Gibco).

The medium can also contain fatty acids or lipids, amino acids (such as non-essential amino acids), vitamin(s), growth factors, cytokines, antioxidant substances, 2-mercaptoethanol, pyruvic acid, buffering agents, and inorganic salts. The concentration of 2-mercaptoethanol can be, for example, about 0.05 to 1.0 mM, and particularly about 0.1 to 0.5, or 0.01, 0.02, 0.03, 0.04, 0.05, 0.1, 0.2, 0.5, 0.8, 1, 1.5, 2, 2.5, 5, 7.5, 10 mM or any intermediate values, but the concentration is particularly not limited thereto as long as it is appropriate for culturing the stem cell(s).

The time for priming of pluripotent stem cells is particularly not limited as long as it is a time duration for which the desired effects such as the improved neural induction can be achieved. For example, the time for priming may be at least or about 10, 15, 20, 25, 30 minutes to several hours (e.g., at least or about one hour, two hours, three hours, four hours, five hours, six hours, eight hours, 12 hours, 16 hours, 24 hours, 36 hours, 48 hours, or any range derivable therein) before dissociation. In other embodiments, the stem cells may be cultured in a priming medium for at least one to five passages.

The density of the pluripotent stem cell(s) to be primed is particularly not limited as far as it is a density at least or about 10, $10^1$, $10^2$, $10^3$, $10^4$, $10^5$, $10^6$, $10^7$, $10^8$ cells/cm$^2$ or at which the desired effects such as the improved neural induction can be achieved. It is, for example, about $1.0 \times 10^4$ to $1.0 \times 10^6$ cells/cm$^2$, more particularly about $2.0 \times 10^4$ to $6.5 \times 10^5$ cells/cm$^2$, and most particularly about $3.0 \times 10^4$ to $3.0 \times 10^5$ cells/cm$^2$.

In certain embodiments, pluripotent stem cells are cultured in a priming medium prior to aggregate formation to improve neural induction (e.g., prior to being dissociated into single cells or small aggregates to induce aggregate formation). In certain embodiments of the invention, the stem cells may be cultured in the absence of feeder cells, feeder cell extracts and/or serum.

B. Culture Conditions

A culture vessel used for culturing the cell(s) can include, but is particularly not limited to: flask, flask for tissue culture, spinner flask, dish, petri dish, dish for tissue culture, multi dish, micro plate, micro-well plate, multi plate, multi-well plate, micro slide, chamber slide, tube, tray, Cell-STACK® Chambers, culture bag, and roller bottle, as long as it is capable of culturing the cells therein. The cells may be cultured in a volume of at least or about 0.2, 0.5, 1, 2, 5, 10, 20, 30, 40, 50, 100, 150, 200, 250, 300, 350, 400, 450, 500, 550, 600, 800, 1000, 1500 mL, or any range derivable therein, depending on the needs of the culture. In a certain embodiment, the culture vessel may be a bioreactor, which may refer to any device or system that supports a biologically active environment. The bioreactor may have a volume of at least or about 2, 4, 5, 6, 8, 10, 15, 20, 25, 50, 75, 100, 150, 200, 500 liters, 1, 2, 4, 6, 8, 10, 15 cubic meters, or any range derivable therein.

The culture vessel surface can be prepared with cellular adhesive or not depending upon the purpose. The cellular adhesive culture vessel can be coated with any substrate for cell adhesion such as extracellular matrix (ECM) to improve the adhesiveness of the vessel surface to the cells. The substrate used for cell adhesion can be any material intended to attach stem cells or feeder cells (if used). Non-limiting substrates for cell adhesion include collagen, gelatin, poly-L-lysine, poly-D-lysine, poly-D-ornithine, laminin, vitronectin, and fibronectin and mixtures thereof, for example, protein mixtures from Engelbreth-Holm-Swarm mouse sarcoma cells (such as Matrigel™ or Geltrex) and lysed cell membrane preparations (Klimanskaya et al., 2005).

Other culturing conditions can be appropriately defined. For example, the culturing temperature can be about 30 to 40° C., for example, at least or about 31, 32, 33, 34, 35, 36, 37, 38, 39° C. but particularly not limited to them. The $CO_2$ concentration can be about 1 to 10%, for example, about 2 to 7%, or any range derivable therein. The oxygen tension can be at least or about 1, 5, 8, 10, 20%, or any range derivable therein.

An adhesion culture may be used in certain aspects. In this case, the cells can be cultured in the presence of feeder cells. In the case where the feeder cells are used in the methods of the present invention, stromal cells such as fetal fibroblasts can be used as feeder cells (for example, refer to; Manipulating the Mouse Embryo A Laboratory Manual (1994); Gene Targeting, A Practical Approach (1993); Martin (1981); Evans et al. (1981); Jainchill et al., (1969); Nakano et al., Science (1996); Kodama et al. (1982); and International Publication Nos. 01/088100 and 2005/080554).

In other aspects, a suspension culture may be used. A suspension culture may include a suspension culture on carriers (Fernandes et al., 2007) or gel/biopolymer encapsulation (United States Patent Publication No. 2007/0116680). The suspension culture of the stem cells means that the stem cells are cultured under non-adherent conditions with respect to the culture vessel or feeder cells (if used) in a medium. The suspension culture of stem cells includes a dissociation culture of stem cells and an aggregate suspension culture of stem cells. The dissociation culture of stem cells means that suspended stem cells are cultured, and the dissociation culture of stem cells include those of single stem cells or those of small cell aggregates composed of a plurality of stem cells (for example, about 2 to 400 cells). When the aforementioned dissociation culture is continued, the cultured, dissociated cells form a larger aggregate of stem cells, and thereafter an aggregate suspension culture can be performed. The aggregate suspension culture includes an embryoid culture method (see Keller et al., 1995), and a SFEB (serum-free embryoid body) method (Watanabe et al., 2005); International Publication No. 2005/123902).

C. Culturing of Pluripotent Stem Cells

Methods for preparing and culturing pluripotent stem cells such as ES cells can be found in standard textbooks and reviews in cell biology, tissue culture, and embryology, including teratocarcinomas and embryonic stem cells: A practical approach (1987); Guide to Techniques in Mouse Development (1993); Embryonic Stem Cell Differentiation in vitro (1993); Properties and uses of Embryonic Stem Cells: Prospects for Application to Human Biology and Gene Therapy (1998), all incorporated herein by reference. Standard methods used in tissue culture generally are described in Animal Cell Culture (1987); Gene Transfer Vectors for Mammalian Cells (1987); and Current Protocols in Molecular Biology and Short Protocols in Molecular Biology (1987 & 1995).

After somatic cells are introduced into or contacted with reprogramming factors, these cells may be cultured in a medium sufficient to maintain the pluripotency and the undifferentiated state. Culturing of induced pluripotent stem (iPS) cells can use various medium and techniques developed to culture primate pluripotent stem cells, more specially, embryonic stem cells, as described in U.S. Pat. Publication 2007/0238170 and U.S. Pat. Publication 2003/0211603, and U.S. Pat. Publication 2008/0171385, which are hereby incorporated by reference. It is appreciated that additional methods for the culture and maintenance of pluripotent stem cells, as would be known to one of skill, may be used with the present invention.

In certain embodiments, undefined conditions may be used; for example, pluripotent cells may be cultured on fibroblast feeder cells or a medium that has been exposed to fibroblast feeder cells in order to maintain the stem cells in an undifferentiated state. Alternately, pluripotent cells may be cultured and maintained in an essentially undifferentiated state using defined, feeder-independent culture system, such as a TeSR medium (Ludwig et al., 2006a; Ludwig et al., 2006b) or E8 medium (Chen et al., 2011: PCT/US2011/046796). Feeder-independent culture systems and media may be used to culture and maintain pluripotent cells. These approaches allow human pluripotent stem cells to remain in an essentially undifferentiated state without the need for mouse fibroblast "feeder layers." As described herein, various modifications may be made to these methods in order to reduce costs as desired.

Various matrix components may be used in culturing, maintaining, or differentiating human pluripotent stem cells. For example, collagen IV, fibronectin, laminin, and vitronectin in combination may be used to coat a culturing surface as a means of providing a solid support for pluripotent cell growth, as described in Ludwig et al. (2006a; 2006b), which are incorporated by reference in their entirety.

Matrigel™ may also be used to provide a substrate for cell culture and maintenance of human pluripotent stem cells. Matrigel™ is a gelatinous protein mixture secreted by mouse tumor cells and is commercially available from BD Biosciences (New Jersey, USA). This mixture resembles the complex extracellular environment found in many tissues and is used by cell biologists as a substrate for cell culture.

D. ROCK Inhibitors and Myosin II inhibitors

Pluripotent stem cells, especially human ES cells and iPS cells, are vulnerable to apoptosis upon cellular detachment and dissociation, which are important for clonal isolation or expansion and differentiation induction. For deriving a stem cell clone for differentiation, ROCK inhibitors or myosin II inhibitors may be used to increase cloning efficiency.

Recently, a small class of molecules have been found to increase cloning efficiency and survival of dissociated pluripotent stem cells, such as Rho-associated kinase (ROCK) inhibitors, which are inhibitors for ROCK-related signaling pathways, for example, Rho-specific inhibitors, ROCK-specific inhibitors or myosin II-specific inhibitors. In certain aspects of the invention, ROCK inhibitors may be used for culturing and passaging of pluripotent stem cells and/or differentiation of the stem cells. Therefore, ROCK inhibitors could be present in any cell culture medium in which pluripotent stem cells grow, dissociate, form aggregates, or undergo differentiation, such as an adherent culture or suspension culture.

ROCK signaling pathways may include Rho family GTPases, ROCK (a major effector kinase downstream of Rho), Myosin II (the predominant effector downstream of ROCK) (Harb et al., 2008), and any intermediate, upstream, or downstream signal processors. ROCK may phosphorylate and inactivate myosin phosphatase target subunit 1 (MYPT1), one of the major downstream targets of ROCK that negatively regulates myosin function through dephosphorylation of myosin regulatory light chain (MRLC).

Rho-specific inhibitors, such as Clostridium botulinum C3 exoenzyme, and/or Myosin II-specific inhibitors may also be used as a ROCK inhibitor in certain aspects of the invention. Unless otherwise stated herein, myosin II inhibitors, such as blebbistatin, can substitute for the experimental use of ROCK inhibitors.

Myosin II was first studied for its role in muscle contraction, but it functions also in non-muscle cells. Myosin II (also known as conventional myosin) contains two heavy chains, each about 2000 amino acids in length, which constitute the head and tail domains. Each of these heavy chains contains the N-terminal head domain, while the C-terminal tails take on a coiled-coil morphology, holding the two heavy chains together (imagine two snakes wrapped around each other, such as in a caduceus). Thus, myosin II has two heads. It also contains 4 light chains (2 per head), which bind the heavy chains in the "neck" region between the head and tail. These light chains are often referred to as the essential light chain and the regulatory light chain. An exemplary Myosin II-specific inhibitor may be Blebbistatin or an analog thereof.

ROCKs are serine/threonine kinases that serve as target proteins for Rho (of which three isoforms exist—RhoA, RhoB and RhoC). Theses kinases were initially characterized as mediators of the formation of RhoA-induced stress fibers and focal adhesions. The two ROCK isoforms—ROCK1 (p160ROCK, also called ROKβ) and ROCK2 (ROKα)—are comprised of a N-terminal kinase domain, followed by a coiled-coil domain containing a Rho-binding domain and a pleckstrin-homology domain (PH). Both ROCKs are cytoskeletal regulators, mediating RhoA effects on stress fiber formation, smooth muscle contraction, cell adhesion, membrane ruffling and cell motility. ROCKs may exert their biological activity by targeting downstream molecules, such as myosin II, myosin light chain (MLC), MLC phosphatase (MLCP) and the phosphatase and tensin homolog (PTEN).

An exemplary ROCK-specific inhibitor is Y-27632, which selectively targets ROCK1 (but also inhibits ROCK2), as well as inhibits TNF-α and IL-1β. Other ROCK inhibitors include, e.g., H-1152, Y-30141, Wf-536, HA-1077, hydroxyl-HA-1077, GSK269962A and SB-772077-B. Doe et al. (2007); Ishizaki et al., supra; Nakajima et al. (2003); and Sasaki et al. (2002), each of which is incorporated herein by reference as if set forth in its entirety.

Other non-limiting examples of ROCK inhibitors include antisense nucleic acid for ROCK, RNA interference inducing nucleic acid (for example, siRNA), competitive peptides, antagonist peptides, inhibitory antibodies, antibody-ScFV fragments, dominant negative variants and expression vectors thereof. Further, since other low molecular compounds are known as ROCK inhibitors, such compounds or derivatives thereof can also be used in embodiments (for example, refer to U.S. Patent Publication Nos. 20050209261, 20050192304, 20040014755, 20040002508, 20040002507, 20030125344 and 20030087919, and International Patent Publication Nos. 2003/062227, 2003/059913, 2003/062225, 2002/076976 and 2004/039796, which are hereby incorporated by reference). In certain aspects of the present invention, a combination of one or two or more of the ROCK inhibitors can also be used.

According to some embodiments, the stem cell can be treated with a ROCK inhibitor or myosin II inhibitor in a medium. Thereby, the medium used in the methods of the present invention may already contain the ROCK inhibitor or Myosin II inhibitor or alternatively, the methods of the present invention may involve a step of adding the ROCK inhibitor or myosin II inhibitor to the medium. The concentration of the ROCK inhibitor or myosin II inhibitor in the medium is particularly not limited as far as it can achieve the desired effects such as the improved survival rate of stem cells. A ROCK inhibitor or myosin II inhibitor, e.g., Y-27632, HA-100, HA-1077, H-1152, or blebbistatin, may be used at an effective concentration of at least or about 0.02, 0.05, 0.1, 0.2, 0.5, 1, 2, 3, 4, 5, 10, 15, 20, 25, 30, 35, 40, 45, 50, 100, 150, 200, 500 to about 1000 µM, or any range derivable therein. These amounts may refer to an amount of a ROCK inhibitor or myosin II inhibitor individually or in combination with one or more ROCK inhibitors or myosin II inhibitors.

The time for treating with the ROCK inhibitor or myosin II inhibitor is particularly not limited as long as it is a time duration for which the desired effects such as the improved survival rate of stem cells can be achieved. For example, the stem cells are maintained in the presence of a ROCK inhibitor or myosin II inhibitor for at least or about 10, 15, 20, 25, 30 minutes to several hours (e.g., at least or about one hour, two hours, three hours, four hours, five hours, six hours, eight hours, 12 hours, 16 hours, 24 hours, 36 hours, 48 hours, or any range derivable therein) before dissociation. After dissociation, the pluripotent stem cell can be treated with the ROCK inhibitor or myosin II inhibitor for, for example, at least or about 2, 3, 4, 5, 6, 7, 8, 9, 10, 11, 12, 16, 24, 48 hours or more to achieve the desired effects.

In other embodiments, the stem cells are maintained in the presence of a ROCK inhibitor or myosin II inhibitor for at least one to five passages. Optionally, the ROCK inhibitor or myosin II inhibitor is subsequently withdrawn from the culture medium, for example after about 4, 8, 12 hours or after about 2, about 4, or about 6 days, or any range derivable therein. In other embodiments, the ROCK inhibitor or myosin II inhibitor is withdrawn after at least one, two, three, four, five passages or more, or any range derivable therein.

The density of the stem cell(s) to be treated with the ROCK inhibitor or myosin II inhibitor is particularly not limited as far as it is a density at which the desired effects such as the improved survival rate of stem cells can be achieved. It is, for example, about $1.0 \times 10^1$ to $1.0 \times 10^7$ cells/mL, more particularly about $1.0 \times 10^2$ to $1.0 \times 10^7$ cells/mL, further more particularly about $1.0 \times 10^3$ to $1.0 \times 10^7$ cells/mL, and most particularly about $3.0 \times 10^4$ to $2.0 \times 10^6$ cells/mL.

In certain embodiments, stem cells are cultured in the presence of ROCK inhibitors or myosin II inhibitors to improve survival at low density (dissociated into single cells or small aggregates), cloning efficiency or passaging efficiency. In certain embodiments of the invention, the stem cells are cultured in the absence of feeder cells, feeder cell extracts and/or serum. The stem cells can be cultured in the presence of a ROCK inhibitor or myosin II inhibitor prior to subcloning or passaging, e.g., for at least one hour before subcloning or passaging. Alternatively or additionally, the stem cells are maintained in the presence of a ROCK inhibitor or myosin II inhibitor during or after subcloning or passaging.

The stem cells to be treated with a ROCK inhibitor or myosin II inhibitor can be dissociated cells or non-dissociated cells after priming of the cells to improve neural induction. The dissociated cells refer to cells treated to promote cell dissociation (for example, the dissociation described later). Dissociated cells include a single cell and cells having formed a small cell clump (aggregate) of several (typically about 2 to 50, 2 to 20, or 2 to 10) cells. The dissociated cells can be suspended (floating) cells or adhered cells. For example, it has been known that ES cells such as human ES cells are susceptible to specific conditions such as dissociation (and/or suspension culture after dissociation).

Certain aspects of the present invention can further involve a step of dissociating stem cells. Stem cell dissociation can be performed using any known procedures. These procedures include treatments with a chelating agent (such as EDTA), an enzyme (such as trypsin, collagenase), or the like, and operations such as mechanical dissociation (such as pipetting). The stem cell(s) can be treated with the ROCK inhibitor or myosin II inhibitor before and/or after dissociation. For example, the stem cell(s) may be treated only after dissociation.

E. Single Cell Passaging

In some embodiments of pluripotent stem cell culturing, once a culture container is full, the colony is split into aggregated cells or even single cells by any method suitable for dissociation, which cells are then placed into new culture containers for passaging. Cell passaging or splitting is a technique that enables cells to survive and grow under cultured conditions for extended periods of time. Cells typically would be passaged when they are about 70%-100% confluent.

Single-cell dissociation of pluripotent stem cells followed by single cell passaging may be used in the present methods with several advantages, like facilitating cell expansion, cell sorting, and defined seeding for differentiation and enabling automatization of culture procedures and clonal expansion. For example, progeny cell clonally derivable from a single cell may be homogenous in genetic structure and/or synchronized in cell cycle, which may increase targeted differentiation. Exemplary methods for single cell passaging may be as described in U.S. Pat. App. 2008/0171385, which is incorporated herein by reference.

In certain embodiments, pluripotent stem cells may be dissociated into single individual cells, or a combination of single individual cells and small cell clusters comprising 2, 3, 4, 5, 6, 7, 8, 9, 10 cells or more. The dissociation may be achieved by mechanical force, or by a cell dissociation agent, such as NaCitrate, or an enzyme, for example, trypsin, trypsin-EDTA, TrypLE Select, or the like.

Based on the source of pluripotent stem cells and the need for expansion, the dissociated cells may be transferred individually or in small clusters to new culture containers in a splitting ratio such as at least or about 1:2, 1:4, 1:5, 1:6, 1:8, 1:10, 1:20, 1:40, 1:50, 1:100, 1:150, 1:200, or any range derivable therein. Suspension cell line split ratios may be done on volume of culture cell suspension. The passage interval may be at least or about every 1, 2, 3, 4, 5, 6, 7, 8, 9, 10, 11, 12, 13, 14, 15, 16, 17, 18, 19, 20 days or any range derivable therein. For example, the achievable split ratios for the different enzymatic passaging protocols may be 1:2 every 3-7 days, 1:3 every 4-7 days, and 1:5 to 1:10 approximately every 7 days, 1:50 to 1:100 every 7 days. When high split ratios are used, the passage interval may be extended to at least 12-14 days or any time period without cell loss due to excessive spontaneous differentiation or cell death.

In certain aspects, single cell passaging may be in the presence of a small molecule effective for increasing cloning efficiency and cell survival, such as a ROCK inhibitor or myosin II inhibitor as described above. Such a ROCK inhibitor or myosin II inhibitor, e.g., Y-27632, HA-1077, H-1152, or blebbistatin, may be used at an effective concentration, for example, at least or about 0.02, 0.05, 0.1, 0.2, 0.5, 1, 2, 3, 4, 5, 10, 15, 20, 25, 30, 35, 40, 45, 50 to about 100 µM, or any range derivable therein.

F. Differentiation of Stem Cells

Methods may be provided to improve neural differentiation efficiency of pluripotent stem cells. Differentiation of pluripotent stem cells can be induced in a variety of manners, such as in attached colonies or by formation of cell aggregates, e.g., in low-attachment environment, wherein those aggregates are referred to as embryoid bodies (EBs). The molecular and cellular morphogenic signals and events within EBs mimic many aspects of the natural ontogeny of such cells in a developing embryo.

Embryoid bodies (EBs) are aggregates of cells derived from pluripotent stem cells, such as ES cells or iPS cells, and have been studied for years with mouse embryonic stem cells. In order to recapitulate some of the cues inherent to in vivo differentiation, certain aspects of the invention may employ three-dimensional aggregates (i.e., embryoid bodies) as an intermediate step. Upon the start of cell aggregation, differentiation may be initiated and the cells may begin to a limited extent to recapitulate embryonic development. Though they cannot form trophectodermal tissue (which includes the placenta), cells of virtually every other type present in the organism can develop. The present invention may further promote neural differentiation following aggregate formation.

Cell aggregation may be imposed by hanging drop, plating upon non-tissue culture treated plates or spinner flasks; either method prevents cells from adhering to a surface to form the typical colony growth. As described above, ROCK inhibitors or myosin II inhibitors may be used before, during or after aggregate formation to culture pluripotent stem cells.

Pluripotent stem cells may be seeded into aggregate promotion medium using any method known in the art of cell culture. For example, pluripotent stem cells may be seeded as a single colony or clonal group into aggregate promotion medium, and pluripotent stem cells may also be seeded as essentially individual cells. In some embodiments, pluripotent stem cells are dissociated into essentially individual cells using mechanical or enzymatic methods known in the art. By way of non-limiting example, pluripotent stem cells may be exposed to a proteolytic enzyme which disrupts the connections between cells and the culturing surface and between the cells themselves. Enzymes which may be used to individualize pluripotent stem cells for aggregate formation and differentiation may include, but are not limited to, trypsin, in its various commercial formulations, such as TrypLE, or a mixture of enzymes such as Accutase®.

In certain embodiments, pluripotent cells may be added or seeded as essentially individual (or dispersed) cells to a culturing medium for culture formation on a culture surface. The culturing medium into which cells are seeded may comprise a medium preferably essentially free of growth factors such as TGFβ and bFGF.

For example, dispersed pluripotent cells are seeded into a culturing medium at a density of from about $10^4$ cells/mL to about $10^{10}$ cells/mL. More particularly, pluripotent cells are seeded at a density of from about $10^5$ cells/mL to about $10^7$ cells/mL, or about $0.5 \times 10^6$ cells/mL to about $3 \times 10^6$ cells/mL. In these embodiments, a culturing surface may be comprised of essentially any material which is compatible with standard aseptic cell culture methods in the art, for example, a non-adherent surface. A culturing surface may additionally comprise a matrix component as described herein. In certain embodiments, a matrix component may be applied to a culturing surface before contacting the surface with cells and medium.

In certain embodiments, adherently cultured pluripotent stem cells may be gradually transitioned to a priming medium essentially free of TGFβ and bFGF. The primed cells can then be induced to associate into aggregates in suspension culture and further differentiated into the neural lineage.

The methods may further comprise differentiation of the cells into astrocytes in vitro. In certain aspects, the novel priming step may enhance neural differentiation more quickly and at higher purity than other neural differentiation procedures. Furthermore, astrocyte formation from primed stem cells is much faster and yields higher purity astrocytes compared to other astrocyte production procedures. Astrocyte differentiation from pluripotent stem cell-derived neural lineage cells can be induced by any method known in the art which activates the cascade of biological events which lead to growth, which include the liberation of inositol triphosphate and intracellular $Ca^{2+}$, liberation of diacyl glycerol and the activation of protein kinase C and other cellular kinases, and the like. Treatment with phorbol esters, differentiation-inducing growth factors and other chemical signals can induce differentiation. Differentiation can also be induced by plating the cells on a fixed substrate such as flasks, plates, or coverslips coated with an ionically charged surface such as poly-L-lysine and poly-L-ornithine and the like.

Other substrates may be used to induce differentiation such as collagen, fibronectin, vitronectin, laminin, matrigel, and the like. Differentiation can also be induced by leaving the cells in suspension in the presence of a proliferation-inducing growth factor, without reinitiating proliferation (i.e., without dissociating the neurospheres).

One illustrative method comprises culturing the cells on a fixed substrate in a culture medium. A proliferation-inducing growth factor can then be administered to the cells. The proliferation inducing growth factor can cause the cells to adhere to the substrate (e.g., polyornithine-treated plastic or glass), flatten, and begin to differentiate into different cell types.

The culture medium can contain 0.5, 1.0, 2.0, 5.0, 10.0, 15.0% (or any range derivable therein) serum such as fetal bovine serum (FBS) to potentiate the formation of astrocytes, but for certain uses, if defined conditions are required, serum would not be used. Within about 20, 30, 40, 50, 60 days after the initiation of further differentiation from aggregates, most or all of the cell progeny may begin to express antigens specific for astrocytes as determined by immunocytochemistry techniques well known in the art.

IV. Signaling Inhibitors

In certain aspects of the invention, TGFβ signaling inhibitors may or may not be used for differentiation of stem cells into neural cells. TGFβ superfamily signaling inhibitors may include, but not be limited to, one or more modulators of signaling pathways of bone morphogenetic protein, ActivinA/Nodal/TGFβ/GDF, vascular endothelial growth factor (VEGF), dickkopf homolog 1 (DKK1), basic fibroblast growth factor (bFGF), insulin growth factor (IGF), and/or epidermal growth factor (EGF).

In particular aspects, the need for addition of TGFβ superfamily signaling inhibitors during differentiation may be obviated by culturing of pluripotent stem cells in a priming culture condition, particularly, a condition essentially free of externally added TGFβ superfamily signaling modulators and bFGF.

In particular aspects, certain pluripotent stem cell lines and clones may require TGFβ superfamily signaling inhibitors to be present during priming, aggregate formation and/or further differentiation for neural differentiation to occur at high purity and efficiency. Furthermore, this requirement may be obviated when FGF8 is included in media at one or more time points in the priming, aggregate formation and/or further differentiation parts of the process.

Stem cells exhibit self-renewing capacity and pluripotency in generating the multitude of embryonic and adult cell types of the metazoan body (reviewed by Rossi et al., 2008). Growth factors, such as Activin/Nodal/TGFβ/GDF and bFGF, regulate stem cell self-renewal and differentiation.

The transforming growth factor beta (TGFβ) superfamily signaling pathway is involved in many cellular processes in both the adult organism and the developing embryo including cell growth, cell differentiation, apoptosis, cellular homeostasis and other cellular functions. In spite of the wide range of cellular processes that the TGFβ superfamily signaling pathway regulates, the process is relatively simple. TGFβ superfamily ligands bind to a type II receptor, which recruits and phosphorylates a type I receptor. The type I receptor then phosphorylates receptor-regulated SMADs (R-SMADs) which can now bind the coSMAD SMAD4. R-SMAD/coSMAD complexes accumulate in the nucleus where they act as transcription factors and participate in the regulation of target gene expression.

Basic fibroblast growth factor, also known as bFGF, FGF2 or FGF-β, is a member of the fibroblast growth factor family. FGF2, the most widely used growth factor that supports mouse and human embryonic stem cell (ESC) self-renewal in culture, induces TGFβ/activin/Nodal/GDF ligands and receptors while suppressing BMP-like activities (Greber et al., 2007; Ogawa et al., 2007). Furthermore, pharmacological inhibitors of the activin/GDF/TGFβ/nodal type I receptor family suppress human and mouse ESC self-renewal (Ogawa et al., 2007). In general, TGFβactivin/Nodal/GDF inhibits differentiation of pluripotent progenitor cells, whereas BMP induces their differentiation (Watabe and Miyazono, 2009).

To promote self-renewal of ESCs, TGFβ/nodal/activin/GDF signaling activates SMAD2 and SMAD3, which directly induce Nanog, one of the crucial stem cell transcription factors (Xu, R. H. et al., 2008). TGFβ superfamily and FGF signaling synergize by enhancing binding of Smad complexes to the Nanog promoter. Interestingly, NANOG provides a molecular link for the antagonism between TGFβ (the self-renewing factor) and BMP (the differentiation factor) in ESCs. Nanog binds to SMAD1, inhibiting its transcriptional activity and limiting the BMP signaling potential that promotes early mesodermal differentiation or tissue-specific differentiation later in development (Suzuki et al., 2006). This example is likely to be expanded to additional regulators of ESC self renewal and differentiation as a result of genome-wide screens for the transcription and signaling factors of these pathways (Chen et al., 2008).

The TGFβ superfamily of ligands include: Bone morphogenetic proteins (BMPs), Growth and differentiation factors (GDFs), Anti-müllerian hormone (AMH), Activin, Nodal and TGFβ's. Signaling begins with the binding of a TGF beta superfamily ligand to a TGF beta type II receptor. The type II receptor is a serine/threonine receptor kinase, which catalyses the phosphorylation of the Type I receptor. Each class of ligand binds to a specific type II receptor. In mammals there are seven known type I receptors and five type II receptors.

There are three activins: Activin A, Activin B and Activin AB. Activins are involved in embryogenesis and osteogenesis. They also regulate many hormones including pituitary, gonadal and hypothalamic hormones as well as insulin. They are also nerve cell survival factors.

The BMPs bind to the Bone morphogenetic protein receptor type-2 (BMPR2). They are involved in a multitude of cellular functions including osteogenesis, cell differentiation, anterior/posterior axis specification, growth, and homeostasis.

The TGF beta family include: TGFβ1, TGFβ2, TGFβ3. Like the BMPS, TGF betas are involved in embryogenesis and cell differentiation, but they are also involved in apoptosis, as well as other functions. They bind to TGF-beta receptor type-2 (TGFBR2).

Nodal binds to activin A receptor, type IIB ACVR2B. It can then either form a receptor complex with activin A receptor, type IB (ACVR1B) or with activin A receptor, type IC (ACVR1C).

The TGF beta superfamily signaling pathway (Table 1) is involved in a wide range of cellular process and subsequently is very heavily regulated. There are a variety of mechanisms that the pathway is modulated both positively and negatively: There are agonists for ligands and R-SMADs; there are decoy receptors; and R-SMADs and receptors are ubiquitinated.

TABLE 1

TGF beta superfamily signaling pathway

| TGF Beta superfamily ligand | Type II Receptor | Type I receptor | R-SMADs | coSMAD | Ligand inhibitors |
|---|---|---|---|---|---|
| Activin A | ACVR2A | ACVR1B (ALK4) | SMAD2, SMAD3 | SMAD4 | Follistatin |

TABLE 1-continued

TGF beta superfamily signaling pathway

| TGF Beta superfamily ligand | Type II Receptor | Type I receptor | R-SMADs | coSMAD | Ligand inhibitors |
|---|---|---|---|---|---|
| GDF1 | ACVR2A | ACVR1B (ALK4) | SMAD2, SMAD3 | SMAD4 | |
| GDF11 | ACVR2B | ACVR1B (ALK4), TGFβRI (ALK5) | SMAD2, SMAD3 | SMAD4 | |
| Bone morphogenetic proteins | BMPR2 | BMPR1A (ALK3), BMPR1B (ALK6) | SMAD1 SMAD5, SMAD8 | SMAD4 | Noggin, Chordin, DAN |
| Nodal | ACVR2B | ACVR1B (ALK4), ACVR1C (ALK7) | SMAD2, SMAD3 | SMAD4 | Lefty |
| TGFβs | TGFβRII | TGFβRI (ALK5) | SMAD2, SMAD3 | SMAD4 | LTBP1, THBS1, Decorin |

As used herein, the term "member of the TGF-β superfamily" or the like refers to growth factors that are generally characterized by one of skill in the art as belonging to the TGF-β superfamily, either due to homology with known members of the TGF-β superfamily, or due to similarity in function with known members of the TGF-β superfamily. In particular embodiments of the invention, if the member of the TGF-β superfamily is present, the TGF-β superfamily member of variant or functional fragment thereof activates SMAD 2 or 3 for the Activin/Nodal/TGFβ/GDF branch and activates SMAD1, 5 or 8 for the BMP branch. In certain embodiments, the member of the TGF-β superfamily is selected from the group consisting of Nodal, Activin A, Activin B, TGF-β, bone morphogenic protein-2 (BMP2) and bone morphogenic protein-4 (BMP4). In one embodiment, the member of the TGF-β superfamily is Activin A.

In certain embodiments, the compositions and methods comprise a condition in the presence or absence of an inhibitor or an inactivator of Activin/Nodal/TGFβ/GDF signaling. As used herein, an "inhibitor or inactivator of Activin/Nodal/TGFβ/GDF signaling" refers to an agent that antagonizes the activity of one or more Activin/Nodal/TGFβ/GDF proteins or any of their upstream or downstream signaling components through any of its possible signaling pathways. Non-limiting examples include SB-431542.

In certain embodiments, the compositions and methods comprise a condition in the presence or absence of an inhibitor or an inactivator of BMP signaling. As used herein, an "inhibitor or inactivator of BMP signaling" refers to an agent that antagonizes the activity of one or more BMP proteins or any of their upstream or downstream signaling components through any of its possible signaling pathways. The compound(s) used to inactivate BMP signaling can be any compound known in the art, or later discovered. Non-limiting examples of inhibitors of BMP signaling include dorsomorphin, dominant-negative, truncated BMP receptor, soluble BMP receptors, BMP receptor-Fc chimeras, noggin, follistatin, chordin, gremlin, cerberus/DAN family proteins, ventropin, high dose activin, and amnionless.

V. Non-Static Culture

In certain aspects, non-static culture could be used for culturing and differentiation of pluripotent stem cells. Suspension culture can be used to produce large scale of EBs and differentiated cells subsequently; however, static culture has little control over the size and shape of EBs formed, which directly influence yield and quality of cells differentiated therefrom. The non-static culture can be any culture with cells kept at a controlled moving speed, by using, for example, shaking, rotating, or stirring platforms or culture vessels, particularly large-volume rotating bioreactors. The agitation may improve circulation of nutrients and cell waste products and also be used to control cell aggregation by providing a more uniform environment. For example, rotary speed may be set to at least or at most about 25, 30, 35, 40, 45, 50, 75, 100 rpm, or any range derivable therein. The incubation period in the non-static culture for pluripotent stem cells, cell aggregates, differentiated stem cells, or progeny cells derived therefrom, may be at least or about 4 hours, 8 hours, 16 hours, or 1, 2, 3, 4, 5, 6 days, or 1, 2, 3, 4, 5, 6, 7 weeks, or any range derivable therein.

VI. Neuron Lineage Characterization

To identify neural cells, determine differentiation efficiency toward a neural lineage, select for or isolate neural cells, or enrich neural cells, neural lineage characteristics may be assessed (Schwartz et al., 2008).

In particular embodiments, the progenitor neural lineage cells, including the cultured cells, may be characterized by expressing one or more of the detectable markers for nestin, Sox1, Pax6, FORSE-1, N-CAD, CD133, FOXG1 and 3CB2. Such a culture of cells can be produced by the methods described herein or by other methods later developed. In particular embodiments, mature neural cells, including the cultured cells, may be characterized by expressing one or more of the detectable markers for Dcx, MAP-2, Synapsin 1, TuJ1, NSE, Map2a, Gap43, NF, CD24, CDH2/CD325, synaptophysin, and CD56/NCAM. Such a culture of cells can be produced by the methods described herein or by other methods later developed.

Neural cells can be characterized according to a number of phenotypic criteria. The criteria include but are not limited to microscopic observation of morphological features, detection or quantification of expressed cell markers, enzymatic activity, neurotransmitters and their receptors, and electrophysiological function.

Certain cells embodied in this invention have morphological features characteristic of neuronal cells. These features are recognized by those of skill in the art. For example, neurons include small cell bodies, and multiple processes reminiscent of axons and dendrites.

Neural cells can also be characterized according to whether they express phenotypic markers characteristic of particular kinds of neural cells including but not limited to dopaminergic neurons (markers include TH, AaDC, Dat, Otx-2 and VMAT2), cholinergic neurons (markers include NGF, ChAT), GABAergic neurons (markers include GAD67 and vGAT), glutamatergic neurons (markers include vGLUT1), serotonergic neurons, motor neurons (markers include HB9, SMN, ChAT, NKX6), sensory neurons (markers include POU4F1 and peripherin), astrocytes (markers include GFAP and Tapal), and oligodendrocytes (markers include O1, O4, CNPase, and MBP).

Also characteristic of specific neural subtypes, particularly terminally differentiated cells like dopaminergic, GABAergic, glutamatergic, serotonergic, and cholinergic neurons, are receptors and enzymes involved in the biosynthesis, release, and reuptake of neurotransmitters, and ion channels involved in the depolarization and repolarization events that relate to synaptic transmission. Evidence of synapse formation can be obtained by staining for synaptophysin. Evidence for receptivity to certain neurotransmitters can be obtained by detecting receptors for gamma amino butyric acid (GABA), glutamate, dopamine, 3,4-dihydroxyphenylalanine (DOPA), noradrenaline, acetylcholine, and serotonin.

In a particular aspect, there may be provided methods for providing astrocytes. Astrocytes are a sub-type of glial cells in the central nervous system. They are also known as astrocytic glial cells. Star-shaped, their many processes envelope synapses made by neurons. Astrocytes are classically identified using histological analysis; many of these cells express the intermediate filament glial fibrillary acidic protein (GFAP). Three forms of astrocytes exist in the CNS, fibrous, protoplasmic, and radial. The fibrous glia are usually located within white matter, have relatively few organelles, and exhibit long unbranched cellular processes. This type often has "vascular feet" that physically connect the cells to the outside of capillary wall when they are in close proximity to them. The protoplasmic glia are found in grey matter tissue, possess a larger quantity of organelles, and exhibit short and highly branched tertiary processes. The radial glia are disposed in a plane perpendicular to axis of ventricles. One of their processes about the pia mater, while the other is deeply buried in gray matter. Radial glia are mostly present during development, playing a role in neuron migration. Mueller cells of retina and Bergmann glia cells of cerebellar cortex represent an exception, being present still during adulthood. When in proximity to the pia mater, all three forms of astrocytes send out processes to form the pia-glial membrane VII. Genetic Alteration of Cells The cells of this invention can be made to contain one or more genetic alterations by genetic engineering of the cells either before, during, or after differentiation (US 2002/0168766). A cell is said to be "genetically altered" or "transgenic" when a polynucleotide has been transferred into the cell by any suitable means of artificial manipulation, or where the cell is a progeny of the originally altered cell that has inherited the polynucleotide. For example, the cells can be processed to increase their replication potential by genetically altering the cells to express telomerase reverse transcriptase, either before or after they progress to restricted developmental lineage cells or terminally differentiated cells (US 2003/0022367).

A variety of mechanisms can be employed for genetic engineering of the cells. For example, in the case where integration is at an essentially random site(s) in the genome, a polynucleotide can be introduced in a retroviral vector (e.g., a lentiviral vector), an adeno-associated virus vector (without a functional Rep gene) or as part of a transposon system, such as a piggyBac vector. In other aspects, the polynucleotide is integrated into a selected genomic site, for example, the nucleic acid can be integrated at the AAVS1 integration site (e.g., by use of an adeno-associated virus vector in the presence of a functional Rep gene). Likewise, in certain aspects, integration at a selected genomic site can be by homologous recombination. The efficiency of standard HR in mammalian cells is only $10^{-6}$ to $10^{-9}$ of cells treated (Capecchi, 1990). The use of meganucleases, or homing endonucleases, such as I-SceI have been used to increase the efficiency of HR. Both natural meganucleases as well as engineered meganucleases with modified targeting specificities have been utilized to increase HR efficiency (Pingoud and Silva, 2007; Chevalier et al., 2002). Another path toward increasing the efficiency of HR has been to engineer chimeric endonucleases with programmable DNA specificity domains (Silva et al., 2011). Zinc-finger nucleases (ZFN) are one example of such a chimeric molecule in which Zinc-finger DNA binding domains are fused with the catalytic domain of a Type IIS restriction endonuclease such as FokI (as reviewed in Durai et al., 2005; PCT/US2004/030606). Another class of such specificity molecules includes Transcription Activator Like Effector (TALE) DNA binding domains fused to the catalytic domain of a Type IIS restriction endonuclease such as FokI (Miller et al., 2011: PCT/IB2010/000154). As used herein, integration at a selected genomic site can comprise insertion of the nucleic acid molecules (or a portion thereof) between two contiguous nucleotide positions in the genome or between two nucleotide positions that are not contiguous (e.g., resulting in a replacement of intervening genomic sequences). For example, integration of the nucleic acid at selected genomic sites can comprise replacement of a gene exon, intron, promoter, coding sequence or an entire gene.

The cells of this invention can also be genetically altered in order to enhance their ability to be involved in tissue regeneration, or to deliver a therapeutic gene to a site of administration. For example, a vector is designed using the known encoding sequence for the desired gene, operatively linked to a promoter that is neural specific.

In certain embodiments of the invention, cells containing a desired nucleic acid construct may be identified in vitro or in vivo by including a marker in the expression vector, such as a selectable or screenable marker. Such markers would confer an identifiable change to the cell permitting easy identification of cells containing the expression vector, or help enrich or identify differentiated neural cells by using a tissue-specific promoter. For example, neuron-specific promoters may be used, including but not limited to, TuJ-1, Map-2, Dcx, Synapsin, enolase 2, glial fibrillary acidic protein, or tubulin alpha-1A chain.

Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker. Usually the inclusion of a drug selection marker aids in the cloning and identification of transformants, for example, genes that confer resistance to blasticidin, neomycin, puromycin, hygromycin, DHFR, GPT, zeocin and histidinol are useful selectable markers.

In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as chloramphenicol acetyltransferase (CAT) may be utilized. One of skill in the art would also know how to employ immunologic markers, possibly in conjunction with FACS analysis. The marker may be used so long as it is capable of being expressed simultaneously with the nucleic acid encoding a gene product. Further examples of selectable and screenable markers are well known to one of skill in the art.

VIII. Uses of Neural Cells or Neural Cell Types

The human neural cells (including neural cell types such as astrocytes) produced using the methods of the present invention have a variety of uses. In particular, the neural cells can be used as a source of nuclear material for nuclear transfer techniques, and used to produce cells, tissues or components of organs for transplant. The invention contemplates that the neural cells of the present invention may be used in human cell therapy or human gene therapy to treat a patient having a neural disease or disorder, including but not limited to Parkinson's disease, Huntington's disease, lysosomal storage diseases, multiple sclerosis, memory and behavioral disorders, Alzheimer's disease, epilepsy, seizures, macular degeneration, and other retinopathies.

The cells can also be used in treatment of nervous system injuries that arise from spinal cord injuries, stroke, or other neural trauma or can be used to treat neural disease and damage induced by surgery, chemotherapy, drug or alcohol abuse, environmental toxins and poisoning. The cells are also useful in treatment of peripheral neuropathy such as those neuropathies associated with injury, diabetes, autoimmune disorders or circulatory system disorders. The cells may also be used to treat diseases or disorders of the neuroendocrine system, and autonomic nervous system including the sympathetic and parasympathetic nervous system.

In a preferred embodiment, a therapeutically effective amount of the neural cell or cell culture enriched in neural cells is administered to a patient with a neural disease. As used herein, the term "therapeutically effective amount" refers to that number of cells which is sufficient to at least alleviate one of the symptoms of the neural disease, disorder, nervous system injury, damage or neuropathy.

The neural cells of the invention can also be used in testing the effect of molecules on neural differentiation or survival, in toxicity testing or in testing molecules for their effects on neural or neuronal functions. This could include screens to identify factors with specific properties affecting neural or neuronal differentiation, development, survival, plasticity or function. In this application the cell cultures could have great utility in the discovery, development and testing of new drugs and compounds that interact with and affect the biology of neural stem cells, neural progenitors or differentiated neural or neuronal cell types. The neural cells can also have great utility in studies designed to identify the cellular and molecular basis of neural development and dysfunction including but not limited to axon guidance, neurodegenerative diseases, neuronal plasticity and learning and memory. Such basic neurobiology studies may identify novel molecular components of these processes and provide novel uses for existing drugs and compounds, as well as identify new drug targets or drug candidates.

The neural cell or the human cell culture enriched in neural cells may disperse and differentiate in vivo following brain implantation. In particular, following intraventricular implantation, the cell can be capable of dispersing widely along the ventricle walls and moving to the sub-ependymal layer. The cell can be further able to move into deeper regions of the brain, including into the untreated (e.g., by injection) side of the brain into sites that include but are not limited to the thalamus, frontal cortex, caudate putamen and colliculus. In addition the neural cell or human cell culture enriched in neural cells can be injected directly into neural tissue with subsequent dispersal of the cells from the site of injection. This could include any region, nucleus, plexus, ganglion or structure of the central or peripheral nervous systems.

IX. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Priming of iPS Cells Prior to Differentiation Leads to Greater Neural Induction

Differentiation of pluripotent cell cultures into functional neurons by suspension culture of cell aggregates or embryoid bodies (EB) is a highly variable process. Success of neural differentiation with current published methods that use TGFβ inhibitors (e.g., SB-431542; Dorsomorphin or Noggin, which are also BMP inhibitors) is dependent on the cell line and the pluripotent cell culture methods and media used, and can vary from passage to passage.

Figure 1B:
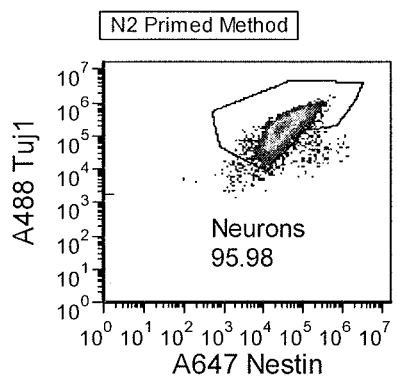
Figure 2A:
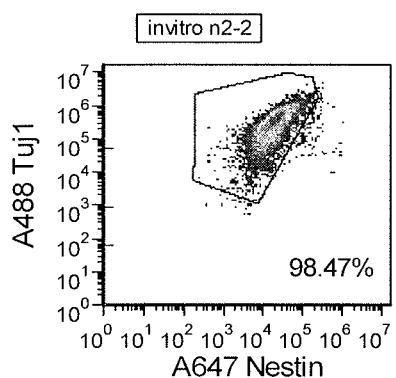
FIGS. 2A-2D: Priming with DMEM-F12 basal medium with N2 supplement from Invitrogen (FIG. 2A), DMEM-F12 basal medium with N2 supplement from Millipore (FIG. 2B), DMEM-F12 basal medium with an Insulin, Transferrin, and Selenium (ITS) supplement (FIG. 2C), and DMEM-F12 basal medium with no supplements (FIG. 2D) all resulted in purities of greater than or equal to 95% neurons as measured by $\beta_{III}$ Tubulin/Nestin flow cytometry. Cultures were analyzed on Day 27.
Figure 2B:
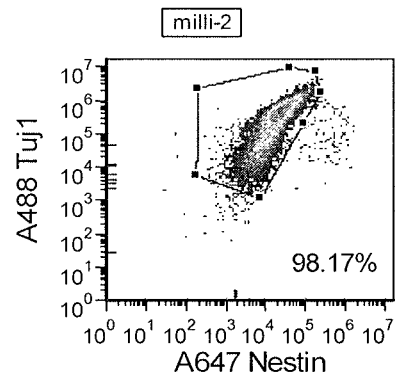
Figure 2C:
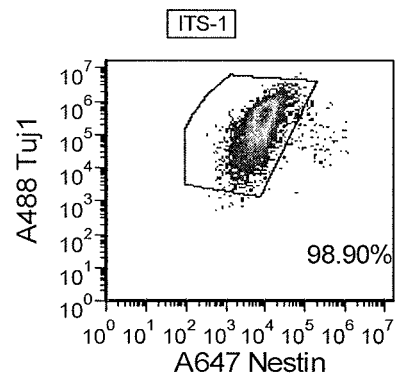
Figure 2D:
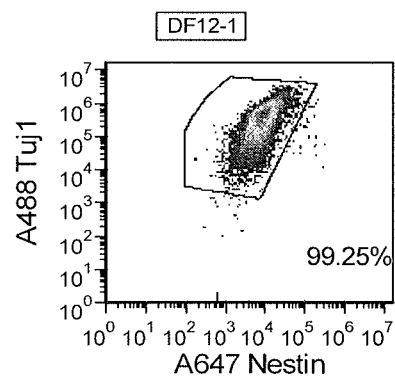

Here pluripotent cells were "primed" in a growth factor-free medium prior to aggregate/EB formation, which resulted in very efficient differentiation (>95% purity) to a neuronal lineage without the use of small molecule inhibitors of the TGF beta superfamily (such as the activin/Nodal/TGFβ/GDF branch and BMP branch). This priming method is in contrast to a method based on published literature using two inhibitors of the TGF beta signaling pathway (a BMP signaling inhibitor and an activin/Nodal/TGFβ/GDF signaling inhibitor: US Patent Publn. 20110229441 and PCT/US2010/024487). FIG. 1A shows the purity of a culture differentiated using methods of forming aggregates in TeSR medium (80% 1× TeSR, 20% TeSR1 5× supplement), transitioning the aggregates into 99% 1× DMEM-F12 with 1% N2 50× supplement medium, and treating the aggregates with 10 µM SB-431542 and 1 µM Dorsomorphin. FIG. 1B shows the purity of a culture produced by priming the pluripotent cells in 90% 1× DMEM-F12 with 1% N2 50× supplement media for three days prior to aggregate formation (Day −3=40% 1× TeSR, 10% TeSR1 5× supplement, 49.5% 1× DMEM-F12, 0.5% N2 100× supplement: Days −2 and −1=99% 1× DMEM-F12, 1% N2 100× supplement). SB431542 and Dorsomorphin were not used. Purity was determined by flow cytometry using $β_{III}$ Tubulin as a committed neuronal marker, and Nestin as a neural progenitor marker.

Example 2

Neural Induction by Priming with DMEM-F12 and N2 Supplement is Due to bFGF and TGF beta Withdrawal Pluripotent cells are usually maintained in mTeSR culture medium, which contains bFGF and TGF beta as the main growth factors for the maintenance of pluripotency. TeSR is comprised of DMEM-F12 as a basal medium, and also contains, in addition to bFGF and TGF beta, Insulin, holo-Transferrin, and Selenium. N2 supplement contains Insulin, holo-Transferrin, Selenium, Progesterone, and Putrescine. The concentrations of the individual components in N2 supplements may vary by supplier. Gradually transitioning pluripotent cells into DMEM-F12 with 1× N2 supplement medium reduces bFGF and TGF beta growth factor availability over time, with little change in other components. The only components present in the DMEM-F12 with 1× N2 supplement medium that are not available in mTeSR at significant levels are Progesterone and Putrescine. To investigate whether a specific component present in the N2 supplement is responsible for the increased neural induction, pluripotent cells were primed for three days as detailed in Example 1 prior to aggregate formation by culturing them in DMEM-F12 medium supplemented with either N2 from various suppliers or a commercially available ITS (Insulin, Transferrin, and Selenium) solution, as well as DMEM-F12 medium alone without additional supplement. Results showed that all conditions that were primed in a 2D format resulted in cultures that exhibited greater than or equal to 95% neurons (FIGS. 2A-2D). These results indicate that the main mechanism of action of priming is the gradual reduction of the bFGF and TGF beta growth factor concentrations prior to 3D aggregate formation.

Example 3

Neuron Production Procedure iPS cells were maintained on Matrigel in TeSR medium (Stem Cell Technologies) and sodium citrate split one passage prior to aggregate formation and grown in T150 flasks, but can be scaled for starting cells in other culture formats. Alternate pluripotent cell culture media (such as E8 media: Chen et al., 2011), containing varying concentrations of TGFβ and/or bFGF, can be used to optimize neural differentiation of different iPS cell lines or clones. Pluripotent cell cultures were then "primed" for differentiation three or four days prior to aggregate formation. Priming of the cells involves gradually transitioning the cells to DMEM-F12 supplemented with 1× N2, which does not contain TGFβ and bFGF. An example of a priming protocol includes culturing the sodium citrate split cells from above for Days −4 and −5 (referenced to the start of aggregate formation) in 80% 1× TeSR/20% TeSR1 5× supplement plus 10 μM blebbistatin, removing the spent media on Day −3 and culturing the cells for 1 day in Neural Transition Media (40% 1× TeSR, 10% TeSR1 5× supplement, 49.5% 1× DMEM-F12, 0.5% N2 100× supplement), and removing the spent media on Day −2 and culturing the cells for Days −2 and −1 in Neural Induction Media (99% 1× DMEM-F 12, 1% N2 100× supplement) with a media change on Day −1. Details for an exemplary neural induction procedure after priming are provided below.

On Day 0 of the neuron differentiation process (specifically, aggregate formation), cells are harvested from T150 flasks (up to five flasks at one time) and, after media is aspirated, 12 mL of warm TrypLE is added to each flask and the cells are incubated at 37° C. for 7 minutes. Meanwhile, one 50 mL conical tube for each T150 is prepared by adding 12 mL 90% 1× DMEM-F12/10% FBS. After a 7 minute incubation, cells are dissociated with gentle trituration into single cell solution and cell solution is transferred into the prepared 50 mL tubes. Cells are centrifuged at 1200 rpm for 5 minutes and the supernatant is aspirated. Each pellet is resuspended in at least 20 mL Aggregate Formation Medium (99% 1× DMEM-F12, 1% N2 100× supplement with 10 μM Blebbistatin). The tubes may be combined and cells are counted (CEDEX HiRES cell counter). Cells are diluted to $1.0 \times 10^6$ cells per mL for both T25 and spinner flasks with Aggregate Formation Media (see above). Concentrated cell suspensions can be directly added to spinner flasks with the appropriate volume of Aggregate Formation Media. Diluted cell stock is counted (CEDEX HiRES cell counter). Five mL of diluted cell stock is dispensed into T25 ULA flasks and 125 mL or 1 L of diluted cell stock is dispensed into 125 mL or 1 L spinner flasks, respectively. Each flask with diluted cells is placed on a rocker or spinner base inside a 37° C. incubator with 7% $CO_2$. Rockers should be rotating at approximately 15 RPM for T25s and spinner flasks should be placed on a magnetic stir platform operating at 70 RPM (for 125 mL spinners) or 40 RPM (for 1L spinners).

On Day 1, cells in T25 flasks are fed by angling each flask on edge in cell culture hood and allowing the suspended aggregates to settle to the bottom of the flask or spinner flask for 10 minutes. Spent media are aspirated and cells are fed with 5 mL of Neural Induction Medium (99% 1× DMEM-F12, 1% N2 100× supplement) for T25s, approximately 100 mL for 125 mL spinner flasks and approximately 800 mL for 1 L spinner flasks. The flasks are returned to the 37° C. incubator with 7% $CO_2$. On each of Days 2 through 6, flasks are handled and media are refreshed the same way. Starting on Day 7, flasks are handled in the same way except cells are fed every other day with fresh Neural Induction Medium. Day 14 is the optimal day of aggregate dissociation and plating of individualized cells to 2D culture vessels. Aggregates are transferred to a conical tube and pelleted with a 30 second spin at 1200 RPM in a centrifuge. The supernatant is aspirated and 1 mL of warm TrypLE per 5 mL of aggregate culture is added and incubated at 37° C. in a waterbath for 5 to 8 minutes. Assess dissociation of the first tube of cells by gently pipetting. If aggregates break apart easily, quench the TrypLE with an equal volume of 90% 1× DMEM-F12/ 10% FBS. If aggregates do not break apart easily, incubate longer and then reassess dissociation followed by quenching. Aggregates are gently dissociated using a P1000 pipetman or serological pipet. The cells are pelleted at 1200 RPM for 5 minutes in a centrifuge. The cells are resuspended in 2.3 mL (or scaled for spinner flasks) of Neural Plating Medium (98% 1× DMEM-F12, 2% B27 50× supplement, 10 μM Blebbistatin). Cells are counted in suspension on CEDEX and the concentration is adjusted to $1.0 \times 10^6$ cells per mL with Neural Plating Medium. Cells are counted again on CEDEX. To each well of a Matrigel coated 6-well plate (seeded at approximately 2 million cells per well), 2 mL of cell suspension are added, which can be scaled appropriately to seed T150 flasks (30 mL) or double CellStacks (260 mL). The day after plating of dissociated aggregates and two days after that (such as, for example, Days 15 and 17), spent media are aspirated and 2D culture vessels are fed Neural Maintenance Medium-Attached (98% DMEM-F1, 2% B27 50× supplement) as follows: 2 mL media per well of a 6 well plate, 30 mL per T150 and 260 mL per double CellSTACK. Following the four days (two feedings) of Neural Maintenance Medium-Attached, cultures are fed once with Neural Maturation Medium #1 (98% 1× DMEM-F12, 2% B27 50× supplement, 2.5 μM DAPT) on Day 19. Cells are harvested on Day 21 using an appropriate volume of warm TrypLE for approximately 6 minutes. Cells are transferred to a conical tube containing equal volume of 90% 1× DMEM-F12/10% FBS. Culture vessel is then rinsed with an equal volume of 90% 1× DMEM-F12/10% FBS to recover additional cells. Cells are pelleted at 1200 RPM for 5 minutes, and the supernatant is aspirated. Cells are resuspended in Neural Plating Medium #2 (97% 1× Neurobasal, 2% B27 50× supplement, 1% Glutamax-I 100× Supplement, 10 μM Blebbistatin) and plated onto a Poly-L-Ornithine/Laminin coated culture vessel at a density of approximately 280 k cells/cm². After 24 hours, media is aspirated and replaced with an equal volume of Neural Maturation Medium #2 (97% 1× Neurobasal, 2% B27 50× supplement, 1% Glutamax-I 100× Supplement, 2.5 μM DAPT). Media exchanges are performed every 48 hours after initial feeding with Neural Maturation Medium #2, until desired neuron maturity is achieved (typically Day 28 or Day 30).

Neurons may be enriched or selected for during the differentiation procedure by utilizing a pluripotent stem cell clone containing an antibiotic resistance gene (such as, for example, a gene conferring resistance to blasticidin, neomycin, puromycin, or hygromycin) or a screenable marker (such as, for example, a fluorescent protein) under the regulation of a neuron specific promoter (such as, for example, DCX, TUJ-1, SYN1, ENO2/NSE, GFAP, TUBA1A or Map-2). At the end of the differentiation procedure (Day 30 to 45), cells are tested for: 1) purity by flow cytometry with βIII-tubulin/Nestin and/or DCX/Nestin double stains, 2) relative composition of neural subtypes (such as, for example, Dopaminergic, GABAergic or Glutamatergic) by immunocytochemistry, and 3) desired neural function by electrophysiology (such as, for example, single cell patch clamp or multielectrode array).

Example 4

Pluripotent Stem Cell Line and Clone Variability

Figure 3A:
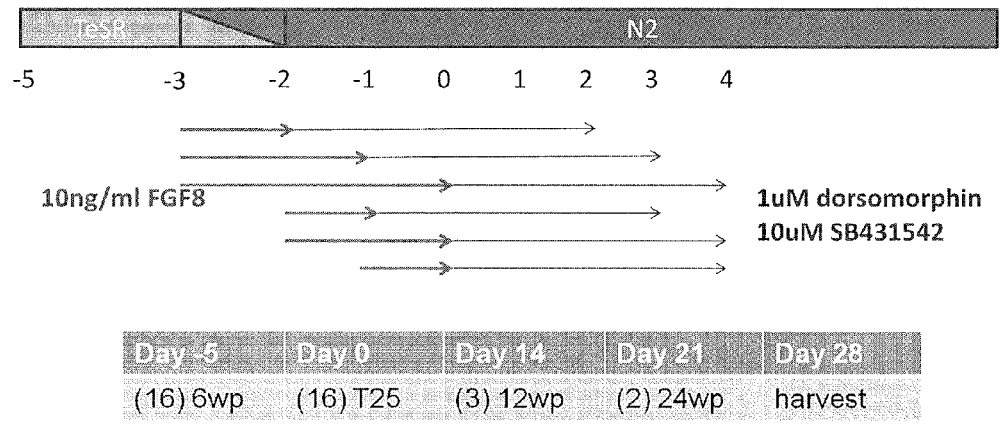
Figure 3B:
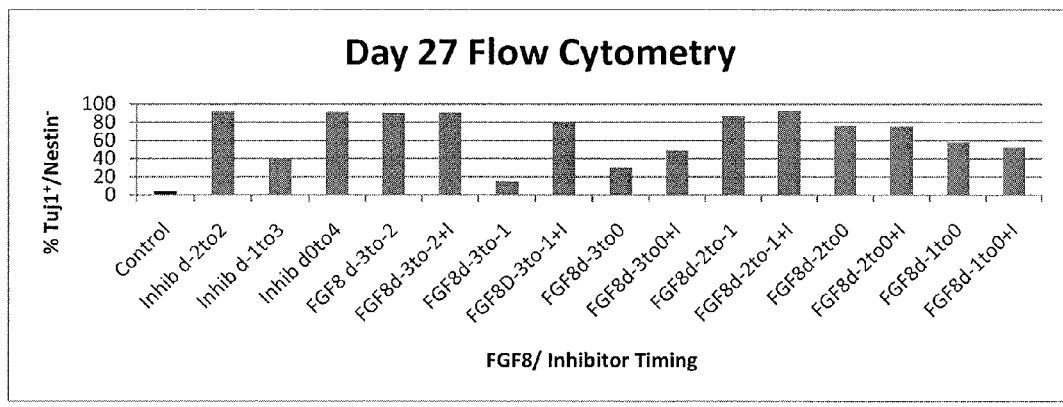

It has been observed that differentiation potential of pluripotent stem cells may be due to line-to-line and even clone-to-clone variability of stem cells' endogenous signaling status. Utilizing the neuron differentiation procedure in Example 3, it has been observed that different pluripotent stem cell lines and clones require the addition of one or more TGFβ superfamily inhibitors and/or FGF8 in the priming media, aggregate formation media and/or further differentiation media to improve differentiation into the neural lineage. FGF signaling has been reported to play an important role in neural induction with FGF8 being reported as an endogenous neural inducer (Sterneckert et al., 2010). Utilizing the procedure detailed in Example 3 above, iPSC line 1729c4 was cultured in cell culture medium also containing 10 µM SB-431542 and/or 1 µM dorsomorphin and/or 10 ng/mL FGF8 during one or more of Days −3, −2, −1, 0, 1, 2, 3 and 4, with Day 0 being the start of aggregate formation (FIG. 3A). At Day 27, cells were tested for purity by flow cytometry with βIII-tubulin/Nestin double stains (FIGS. 3B). In general for this particular iPSC line, conditions containing inhibitors resulted in higher neural lineage purity than without (control Example 3 without inhibitors or FGF8 added) for certain days during priming, aggregate formation, and/or further differentiation. For example, if SB-431542 and dorsomorphin were present during Days −2, −1, 0, and 1 (labeled as "Inhib d-2to2" in FIG. 3B), 92% of the cells were βIII-tubulin/Nestin positive. However, FGF8 could be used instead of inhibitors yielding a neuron culture of high purity (i.e., FGF8 present on Day −3, 90% of cells were βIII-tubulin/Nestin positive). In separate experiments utilizing a different iPSC line (2.042), addition of only one of 10 µM SB-431542 or 1 µM dorsomorphin in medium on Days −2, −1, 0 and 1 resulted in similarly high neuron purities as determined by βIII-tubulin/Nestin double stains compared to when both inhibitors were used (FIG. 3C) whereas the lack of inhibitors (Experiment 3 process control) resulted in a failed differentiation by Day 9. These results suggest that titration experiments utilizing combinations of TGFβ superfamily signaling inhibitors and/or FGF8 as well as conditions lacking both may be an important first step toward optimizing differentiation to the neural lineage for individual pluripotent stem cell lines and clones.

Example 5

Astrocyte Production Procedure

Astrocytes are astroglia found in the central nervous system. They perform a variety of functions including maintaining normal homeostasis in the brain. Anomalies in function of astrocytes have been implicated in a number of disease states. As such, having a readily available source of high purity astrocytes produced by a time efficient procedure could significantly benefit the understanding of the roles of astrocytes and the treatment of neurological disorders and injuries. Methods for producing astrocytes from pluripotent stem cells have been previously reported (Krencik and Zhang, 2011: Krencik et al., 2011). However, many of the protocols are quite lengthy (upwards of 6 months) and/or result in low purities of astrocytes compared to contaminating cells and other neuronal cell types. As such, there is a need for a time efficient procedure for the production of high purity astrocytes.

iPS cell line 8004 was differentiated using the procedure of Example 3 with and without 10 µM SB-431542 added to culture medium on Days −2, −1, 0, and 1. On Day 28, neuron purity as determined by TUJ1/Nestin flow cytometry staining was 80% without SB-431542 and 97% with SB-431542. Beginning on Day 30 of the. procedure, cells were fed 90% 1× DMEM-F12/10% FBS every 7 days. Astrocyte outgrowth was first detected on Day 45. On Day 48, cultures were assayed by flow cytometry for astrocyte purity using GFAP as a marker for astrocytes. The cells cultured without SB-431542 on Days −2, −1, 0, and 1 exhibited 91% GFAP cells (indicative of astrocytes). Interestingly, the cells cultured with added SB-431542 exhibited 56% GFAP positive cells. These results indicate that lower neural cell type purities (as assessed by TUJ1/Nestin flow cytometry staining) earlier in neural lineage differentiation may yield higher purities of astrocytes when cultured under astrocyte conducive conditions. In summary, the methods detailed herein provide for a method to produce cultures of high purity astrocytes in a time efficient manner relative to existing astrocyte differentiation methods.

\*\*\*

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.
U.S. Pat. No. 5,843,780
U.S. Pat. No. 6,200,806
U.S. Pat. No. 6,833,269
U.S. Pat. No. 7,029,913
U.S. Patent Appln. 2008/0171385
U.S. Patent Appln. 61/058,858

U.S. Patent Appln. 61/172,079
U.S. Patent Appln. 61/184,546
U.S. Patent Publn. 2002/0168766
U.S. Patent Publn. 2003/0022367
U.S. Patent Publn. 2003/0211603
U.S. Patent Publn. 20030087919
U.S. Patent Publn. 20030125344
U.S. Patent Publn. 20040002507
U.S. Patent Publn. 20040002508
U.S. Patent Publn. 20040014755
U.S. Patent Publn. 20050192304
U.S. Patent Publn. 20050209261
U.S. Patent Publn. 2007/0116680
U.S. Patent Publn. 2007/0238170
U.S. Patent Publn. 2008/0171385
U.S. Patent Publn. 2011/0229441
PCT/US2010/024487
PCT/US2011/046796
A practical approach, 1987
Andrews et al., In: Teratocarcinomas and Embryonic Stem Cells, Robertson (Ed.), IRL Press, 207-246,1987.
Animal Cell Culture, 1987.
Bottenstein and Sato, Proc. Natl. Acad. Sci. USA, 76:514-517, 1979.
Byrne et al., Nature, 450(7169):497-502, 2007.
Chen et al., Cell, 133:1106-1117, 2008.
Chen et al., Nature Methods 8:424-429, 2011.
Current Protocols in Molecular Biology and Short Protocols in Molecular Biology, 1987 and 1995.
Doe et al., J. Pharmacol. Exp. Ther., 32:89-98, 2007.
Embryonic Stem Cell Differentiation in vitro, 1993.
Evans et. al., Nature, 292:154, 1981.
Fernandes, et al., J. Biotechnology, 132(2):227-236, 2007.
Gene Targeting, A Practical Approach, IRL Press at Oxford University Press, 1993.
Gene Transfer Vectors for Mammalian Cells, 1987.
Greber et al., Stem Cells, 25:455-464, 2007.
Guide to Techniques in Mouse Development, 1993.
Harb et al., PLoS One, 20;3(8):e3001, 2008.
International Patent Publication Nos. 2003/062227, 2003/059913, 2003/062225, 2002/076976 and 2004/039796,
International Publication No. 2005/123902).
International Publication Nos. 01/088100 and 2005/080554
Ishizaki, et al., Mol. Pharmacol., 57:976-983, 2000.
Jainchill et al., J. Virol., 4:549, 1969.
Keller et al., Curr. Opin. Cell Biol., 7:862-869, 1995.
Kim et al, Nature, 418:50-56, 2002.
Klimanskaya et al., Lancet., 365:P1636-1641, 2005.
Kodama et al., J. Cell. Physiol., 112:89, 1982.
Krencik et al., Nature Biotechnology 29:528-534, 2011.
Krencik and Zhang, Nature Protocols 6(11):1710-1717, 2011.
Ludwig et al., Nat. Biotechnol., 24(2):185-187, 2006b.
Ludwig et al., Nat. Methods, 3(8):637-46, 2006a.
Manipulating the Mouse Embryo A Laboratory Manual, Second Edition, Cold Spring Harbor Laboratory Press, 1994.
Martin, Proc. Natl. Acad. Sci. USA, 78:7634, 1981.
Nakajima et al., Cancer Chemother. Pharmacol., 52:319-324, 2003.
Nakano et al., Science, 272, 722, 1996.
Ogawa et al., J. Cell Sci., 120:55-65, 2007.
Properties and uses of Embryonic Stem Cells: Prospects for Application to Human Biology and Gene Therapy, 1998.
Reubinoff et al., Nat. Biotechnol., 18:399-404, 2000.
Sasaki et al., Pharmacol. Ther., 93:225-232, 2002.
Schwartz et al., Methods 45(2): 142-158, 2008.
Smith, In: Origins and Properties of Mouse Embryonic Stem Cells, Annu. Rev. Cell. Dev. Biol., 2000.
Sterneckert et al., Stem Cells, 28:1772-1781, 2010.
Suzuki et al., Proc. Natl. Acad. Sci. USA, 103:10294-10299., 2006.
Takahashi and Yamanaka, Cell, 126:663-676, 2006.
Takahashi et al., Cell, 126(4):663-76, 2007.
Takahashi et al., Cell, 131:861-872, 2007.
Thomson and Marshall, Curr. Top. Dev. Biol., 38:133-165, 1998.
Thomson and Odorico, J. Trends. Biotechnol., 18:53B57, 2000.
Thomson et al. Proc. Natl. Acad. Scie. USA, 92:7844-7848, 1995.
Thomson et al., Science, 282:1145, 1998.
Watabe and Miyazono, Cell Res., 19:103-115, 2009.
Watanabe et al., Nature Neurosci., 8:288-296, 2005.
Xu et al., Cell Stem Cell, 3:196-206., 2008.
Xu et al., Nat. Biotechnol., 19:971-974, 2001.
Yakubov et al., Biochemical and Biophysical Research Communications 394: 189-193, 2010.
Ying et al., Cell, 115:281-292, 2003.
Yu and Thomson, Genes Dev. 22(15):1987-97, 2008.
Yu et al., Science, 318:1917-1920, 2007.
Yu et al., Science, 324(5928):797-801, 2009.

What is claimed is:

1. A method for producing human neural cells, comprising:
   a) culturing a population of human pluripotent stem cells in a medium comprising transforming growth factor β (TGFβ) and basic fibroblast growth factor (bFGF) that maintains cell pluripotency;
   b) priming the pluripotent stem cells, prior to aggregate formation, in an adherent culture and in a serum-free culture medium essentially free of externally added TGFβ and bFGF and in the absence of murine feeder cells;
   wherein priming occurs for at least one day; and
   wherein the levels of TGFβ and bFGF are gradually reduced;
   c) forming aggregates from the cells in step b) in a suspension culture; and
   d) further differentiating the aggregates into a cell population comprising neural cells, thereby producing human neural cells.

2. The method of claim 1, wherein the pluripotent stem cells are induced pluripotent stem (iPS) cells.

3. The method of claim 1, wherein the pluripotent stem cells in step b) are cultured on a non-cellular matrix component.

4. The method of claim 1, wherein the culture medium in the steps of b) priming, c) forming aggregates, and/or at most about the first one, two, three, four, or five days of step d) of further differentiation has an externally added TGFβ superfamily signaling inhibitor and/or FGF8.

5. The method of claim 4, wherein the externally added TGFβ superfamily signaling inhibitor and/or FGF8 is present in an amount determined to be appropriate for differentiation of the population into neural cells, wherein said amount is between about 5 ng/mL and about 200 ng/mL.

6. The method of claim 5, further comprising testing the neural differentiation efficiency to determine the appropriate amount of the externally added TGFβ superfamily signaling inhibitor and/or FGF8 as the amount associated with the highest neural differentiation efficiency for cells from the population.

7. The method of claim 1, wherein the culture medium in the steps of b) priming, c) forming aggregates and/or d) further differentiation does not have an externally added TGFβ superfamily signaling inhibitor and/or FGF8.

8. The method of claim 4, wherein TGFβ superfamily signaling inhibitor is a BMP signaling inhibitor and/or Activin/Nodal/TGFβ/GDF signaling inhibitor.

9. The method of claim 1, wherein the culture medium in step b) is chemically-defined.

10. The method of claim 9, wherein the culture medium in step b) is a Dulbecco's Modified Eagle Medium with nutrient mixture F-12 (DMEM/F12), a DMEM-F12 medium with B-27 supplement, a DMEM-F12 medium with N2 supplement, or a DMEM-F12 medium with an insulin, transferrin, and selenium (ITS) supplement.

11. The method of claim 1, wherein the priming in step b) is for a time period from about one day to about 5 days prior to aggregate formation.

12. The method of claim 1, further comprising dissociating the cells from step b) from one another into essentially single cells prior to forming aggregates.

13. The method of claim 1, wherein the aggregates are formed in an aggregate formation medium essentially free of externally added TGFβ and bFGF.

14. The method of claim 1, wherein the formed aggregates have an average size of about 10 to 400 μm in diameter.

15. The method of claim 1, wherein the aggregates are formed in an aggregate formation medium comprising an externally added myosin II inhibitor and/or Rho-associated kinase (ROCK) inhibitor.

16. The method of claim 1, wherein the suspension culture has a volume of from about 5 milliliters to about 25 liters.

17. The method of claim 1, wherein the suspension culture is rotated or shaken at a speed of about 15 rpm to about 100 rpm.

18. The method of claim 1, wherein the cell population comprises at least about 90% neural cells.

19. The method of claim 18, wherein the cell population comprises at least about 95% neural cells.

20. The method of claim 1, further comprising enriching or isolating neural cells.

21. The method of claim 1, comprising further differentiating the population comprising neural cells into a second population comprising astrocytes.

22. The method of claim 21, the population comprising neural cells is contacted with a serum to further differentiate into astrocytes.

23. The method of claim 22, wherein the culture medium in the steps of b) priming, c) forming aggregates and d) further differentiation does not have an externally added TGFβ superfamily signaling inhibitor and/or FGF8.

24. The method of claim 21, wherein the second cell population comprises at least about 90% astrocytes at a time prior to day 90 of differentiation.

25. The method of claim 21, wherein the second cell population comprises at least about 90% astrocytes at a time prior to day 50 of differentiation.

26. The method of claim 21, further comprising enriching or isolating astrocytes.

27. A method for treating a subject having a neural disease, comprising administering to the subject a therapeutically effective amount of the neural cells prepared by the method of claim 1 or astrocytes prepared by the method of claim 21.

* * * * *